(12) United States Patent
Holm-Kennedy

(10) Patent No.: US 7,317,216 B2
(45) Date of Patent: Jan. 8, 2008

(54) ULTRASENSITIVE BIOCHEMICAL SENSING PLATFORM

(75) Inventor: James W. Holm-Kennedy, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 10/976,503

(22) Filed: Oct. 29, 2004

(65) Prior Publication Data

US 2005/0224346 A1 Oct. 13, 2005

Related U.S. Application Data

(60) Provisional application No. 60/516,535, filed on Oct. 31, 2003, provisional application No. 60/516,485, filed on Oct. 31, 2003.

(51) Int. Cl.
*H01L 23/58* (2006.01)
(52) U.S. Cl. .................. 257/253; 435/7.1; 435/287.2; 435/173.4; 435/477
(58) Field of Classification Search .............. 257/253, 257/414, 40; 435/7.9
See application file for complete search history.

(56) References Cited

U.S. PATENT DOCUMENTS

| | | |
|---|---|---|
| 4,885,623 A | 12/1989 | Holm-Kennedy et al. |
| 4,916,505 A | 4/1990 | Holm-Kennedy |
| 4,926,682 A | 5/1990 | Holm-Kennedy et al. |
| 4,926,693 A | 5/1990 | Holm-Kennedy et al. |
| 4,951,510 A | 8/1990 | Holm-Kennedy et al. |
| 4,960,177 A | 10/1990 | Holm-Kennedy et al. |
| 5,036,286 A | 7/1991 | Holm-Kennedy et al. |
| 5,083,466 A | 1/1992 | Holm-Kennedy et al. |
| 5,095,762 A | 3/1992 | Holm-Kennedy et al. |
| 5,101,669 A | 4/1992 | Holm-Kennedy et al. |
| 5,140,393 A | 8/1992 | Hijikihigawa et al. |
| 5,466,348 A | 11/1995 | Holm-Kennedy |
| 5,784,507 A | 7/1998 | Holm-Kennedy et al. |
| 6,280,586 B1 * | 8/2001 | Wolf et al. .................. 257/253 |
| 6,531,364 B1 * | 3/2003 | Gardner et al. ............. 438/287 |
| 2004/0023476 A1 * | 2/2004 | Ballantine et al. .......... 438/585 |

FOREIGN PATENT DOCUMENTS

| | | | |
|---|---|---|---|
| DE | 4028062 | * | 3/1992 |
| JP | 55-010546 A | | 1/1980 |
| JP | 08-313476 A | | 11/1996 |
| JP | 10-260156 | * | 9/1998 |
| WO | WO 01/64945 A2 | | 9/2001 |

* cited by examiner

*Primary Examiner*—Evan Pert
*Assistant Examiner*—Tan Tran
(74) *Attorney, Agent, or Firm*—James Creighton Wray; Clifford D. Hyra

(57) ABSTRACT

An electronic sensor is provided for detecting the presence of one or more targets of interest in a sample. The sensor preferably comprises a special type of field effect transistor in which conductance is enhanced by target binding to recognition elements in the active region. An array of sensors may be formed to analyze a sample for multiple targets. The sensor may be used, for example, to detect the presence of pathogens, polypeptides, nucleic acids, toxins and other biochemical and chemical agents. The sensor is useful in a wide variety of applications including medical diagnostics, agriculture, public health, environmental monitoring and biomedical research.

34 Claims, 41 Drawing Sheets

| Symbol | Description |
|---|---|
| Y | = Receptor to target #1 |
| ⊥ | = Receptor to target #2 |
| Y | = Receptor to target #3 |
| W | = Receptor to target #4 |
| Y | = Receptor to target #5 |
| E | = Receptor to target #6 |
| ■ | = Target antigen or chemical |

ULTRASENSITIVE BIOCHEMICAL SENSING PLATFORM

REFERENCE TO RELATED APPLICATIONS

The present claims priority under 35 U.S.C. §119(e) to U.S. Provisional Application Nos. 60/516,485, and 60/516,535, both of which were filed Oct. 31, 2003.

FIELD OF THE INVENTION

The present invention relates to a sensor for the detection of targets in a sample. In particular it relates to sensors comprising integrated circuits with semiconductor device sensors that can detect the binding of one or more targets of interest to recognition elements on the active region of the sensor surface.

BACKGROUND OF THE INVENTION

The detection, identification and quantification of target molecules in a sample has a wide variety of applications in many fields. For example, in medical diagnostics it is desirable to be able to screen bodily fluids, such as blood, for the presence of particular targets that may be indicative of a disease or disorder. In other areas, such as bioterror and environmental remediation, it is important to be able to identify the presence of toxic compounds or infectious agents in the environment.

Sensors for identifying targets of interest may be based on or related to transistor principles used for electronic devices in integrated circuits. One such sensor is described in U.S. Pat. No. 5,466,348, which is incorporated by reference herein in its entirety.

SUMMARY OF THE INVENTION

In one aspect of the present invention a sensor is provided for detecting the presence of a target in a sample. The sensor may be used, for example, to detect the presence of toxins, pathogens, disease markers, nucleic acids, proteins, enzymes or other molecules or complexes in a sample.

The sensor preferably comprises a recognition element for the target of interest bound to the active region of a field effect transistor (FET). The active region, in turn, overlies a conducting p channel connecting a source and drain region. Typically this channel is a conducting channel. The channel may be a p-channel or an n-channel. Thus, the sensor typically operates in accumulation mode upon binding of a negatively charged target. A negatively charged target will increase the conductance of the p channel. However, in other embodiments the sensor acts in depletion mode. The sensitivity of the sensor may be increased by applying a reverse bias to a back gate underlying or to the side of the channel.

In a preferred embodiment, recognition elements are dispersed in a material matrix, such as in a gel or attached to a membrane.

In some embodiments, the active region comprises a gate electrode, such as a polysilicon or conducting gate, over a gate dielectric layer. A recognition element is bound to the polysilicon or conducting gate or associated with the gate in a matrix material such as a gel. In other embodiments, a conducting gate electrode is not present and the recognition element is bound to or associated with the dielectric layer, for example a silicon nitride layer.

The recognition element is preferably selected from the group consisting of antibodies, antibody fragments, peptides, oligonucleotides, DNA, RNA, aptamers, proteins, viruses, enzymes, receptors, bacteria, cells, cell fragments, inorganic molecules, organic molecules and combinations thereof.

In another aspect of the invention an array of two or more sensors is provided. The sensors may be utilized to detect multiple targets. In one embodiment, a first sensor detects the presence of one target while a second sensor detects the presence of a second target of interest. The second target of interest may provide confirmation of the presence of the first target of interest.

In another aspect, a method for identifying the presence of one or more targets in a sample is provided. The active region of a sensor is contacted with the sample and sensor output is measured. An electrode is provided at a first distance from the active region. The electrode is not functionally tied to the sensor, but generates an electric field in the sample that increases target concentration in the vicinity of the sensor. In one embodiment the electric field does not terminate on the sensor.

The presence of a target of interest in the sample is identified where the sensor output indicates a change in the conductance of the channel upon contacting the sample. The sensor output is preferably a measure of conductance, transconductance, voltage, current or resistance. The change of conductance resulting from target binding may be enhanced by contacting the bound target with a secondary charged particle or with a particle providing an additional contact potential contribution. A secondary charged particle may be, for example, a molecule, a protein, such as an enzyme, an antibody, a cell or cell fragment, a nucleic acid, including RNA, DNA and cDNA, bacteria, a virus, a bead, a nanoparticle or a nanotube. The bead may be coated with another material, preferably a charge carrying substance such as a detergent. A secondary contact potential contributing particle may be a metallic bead.

Preferably, the sensor comprises one or more recognition elements for the target of interest bound to the active region. The active region overlies a p or n conducting channel connecting a source and drain region. The source and drain region are typically n or p doped to provide an ohmic contact to the channel.

According to another aspect of the invention, a sensor is provided for detecting the presence of a target in a sample, where the sensor comprises a field effect transistor operating in an enhancement, accumulation or depletion mode. Binding of the target of interest to recognition elements on the active region of the sensor increases or decreases conduction through a channel connecting a source and drain region. In preferred embodiments, the active region is surrounded by a conducting shield, which prevents undesired interaction with the sample outside of the active area. The conducting shield is preferably arranged parallel to the substrate surface and extends in all directions away from the active region. The conductive shield may comprise any conductive material, preferably a conductive metal or a conductive polymer. In a particular embodiment, the conducting shield is biased with a voltage.

The channel may be a p type conducting channel or an n type conducting channel and the target may be negatively or positively charged. In one embodiment the pH of the sample is adjusted to produce the desired charge on the target. Attachment of the target to the active affects conduction in the channel.

In another aspect, a sensor for detecting the presence of a target of interest is provided, where the sensor comprises one or more recognition elements associated with an active region. An electrode is located at a first distance from the active region. The electrode is preferably not functionally tied to the sensor. The electrode may take the form of a grid or a cage. The cage may comprise, for example, a conducting mesh, such as a metal mesh, a conducting polymer mesh or a metal-coated mesh. In a particular embodiment the cage electrode is a stainless steel mesh.

In some embodiments, a second electrode is located at a second distance from the active region of the sensor. The second electrode may also be a grid or cage electrode. Additional electrodes may be located at further distances from the active region.

The electrodes preferably generate an electric field that acts on charged target molecules to cause them to drift into the vicinity of the active region. The increased concentration near the active region increases receptor sensitivity and speed.

A single sensor may be used to identify the presence of more than one target in a sample. In one embodiment, the sensor incorporates multiple different recognition elements on the active region. In one embodiment the sensor comprises recognition elements for more than one polynucleotide. In another embodiment the sensor comprises recognition elements for more than one polypeptide. In other embodiments the sensor may comprise recognition elements for two or more different chemicals.

The sensors may be arranged to form an array for detecting the presence of one or more targets in a sample. In one embodiment the array comprises two or more sensors for detecting multiple different toxins in a sample. In another embodiment the array comprises two or more sensors for detecting the multiple disease markers in a sample. In a further embodiment the array comprises two or more sensors with recognition elements for detecting nucleotides or proteins.

The arrays may comprise multiple sensors with the same type of recognition elements or sensors with orthogonal recognition elements for confirming the presence of a particular target. In one embodiment the array comprises a first sensor for detecting the presence of a first target of interest and a second sensor for detecting the presence of a second target. In one embodiment, the first and second targets are related and the presence of the second target provides confirmation of the presence of the first target.

BRIEF DESCRIPTION OF THE DRAWINGS

FIG. 1 is a schematic illustration of a sensor incorporating an assortment of different recognition element groups. Here the recognition elements are attached to the active region of a sensor as shown. Each type of recognition elements provides specific binding to at least one specific target molecule. If any of the target molecules are present, binding results in a sensor output signal (signature). In this example, the number of recognition elements specific to each target is assumed to be equal in surface density (recognition element number/square micron). Where a three dimensional arrangement of recognition elements is used, the number of recognition elements specific to each target is assumed to be equal in density.

FIG. 2 is a bar chart showing the sensor output signal upon target binding to the sensor illustrated in FIG. 1. A sensor signal for each different binding target is schematically represented. The dotted lines indicate what the signal output $S_1$ through $S_N$ would be for recognition elements groups $R_1$ through $R_N$ if these recognition elements were fully bound by the specific corresponding target. The solid line represents the signal from the sensor for the second recognition element ($R_2$). The different signal magnitudes arise from different recognition element and target properties such as magnitude of charge and/or chemical potential associated with the bound target.

FIG. 3 schematically illustrates a sensor with adjusted recognition element densities. A sensor surface or region overlaying an active sensor region is shown. Different groups of recognition elements specific to different targets, such as disease markers, and with corresponding different surface or bulk densities, are attached to the chemically active surface or bulk. The recognition element densities for each target are chosen such that the resultant signal for full recognition element binding (saturated binding) to any of the recognition element sets is of approximately the same magnitude regardless of which target is detected in the sample, as indicated by the bar heights in FIG. 4. Equal output heights are indicated if all recognition elements of a particular type are bound.

FIG. 4 is a bar graph illustrating the sensor signal output for the recognition element configuration of FIG. 3. Saturated sensor recognition element attachment resulting in a "standard" reference signal amplitude is shown by the first bar in the sequence. The sensor output signal amplitude is the same for each target in this design. Here, the second recognition element group ($R_2$) is fully bound by its target, producing the signal indicated by the solid bar, with only that target present in the sample. The remaining recognition elements ($R_1$, $R_3$, $R_4$) remain unbound with zero contribution to the output signal, as indicated by the dotted bars. Target identification corresponds to output signal strength.

FIG. 5 is a bar graph illustrating signal output from a sensor configured to detect multiple targets, such as multiple disease indicators. If multiple targets are present for the configuration of FIG. 3, then multiple "standard" amplitudes of approximately equal magnitude will contribute additively to the overall sensor output amplitude. Here, one "unit" of sensor output amplitude $S_D$ indicates a marker for one disease is present, a sensor output signal of $2S_D$ indicates that markers for two diseases are present in the sample, and so on. The sensor thus identifies how many disease related agents are present in the sample. It is assumed that each target density is sufficient to saturate its respective recognition elements.

FIG. 6 is a bar graph illustrating weak signal output resulting from a low target concentration in the sample. In a situation where the concentration of the target is very low, the sensor output signal may be lower than what would be expected for saturation of recognition elements ($S_L<S_D$). This allows the sensor to be used to differentiate between target concentration in a sample. For example, where a disease is in the early stages of development, a disease related target may be present at a lower concentration than when the disease is at a more advanced stage of development.

FIG. 7 shows a schematic cross section of a particular field effect transistor (FET). Here a buried conducting p-channel is formed in an n-Si substrate. The device has voltage tuning of sensor sensitivity via a back gate applied voltage bias. The gate area is represented with a silicon nitride gate dielectric layer which in this example is covered with a polysilicon gate. The nitride layer can also serve as a protective layer over other features in the transistor and is extended far enough from the active area to insure that the active sensor region is completely protected from moisture influences or the influence of other liquid and chemical contamination. Other gate dielectrics may be used.

Recognition elements are attached to the gate. There is no external electrical contact to the gate. That is, the gate is allowed to "float." In other embodiments the conducting channel is an n-channel.

Figure 8:
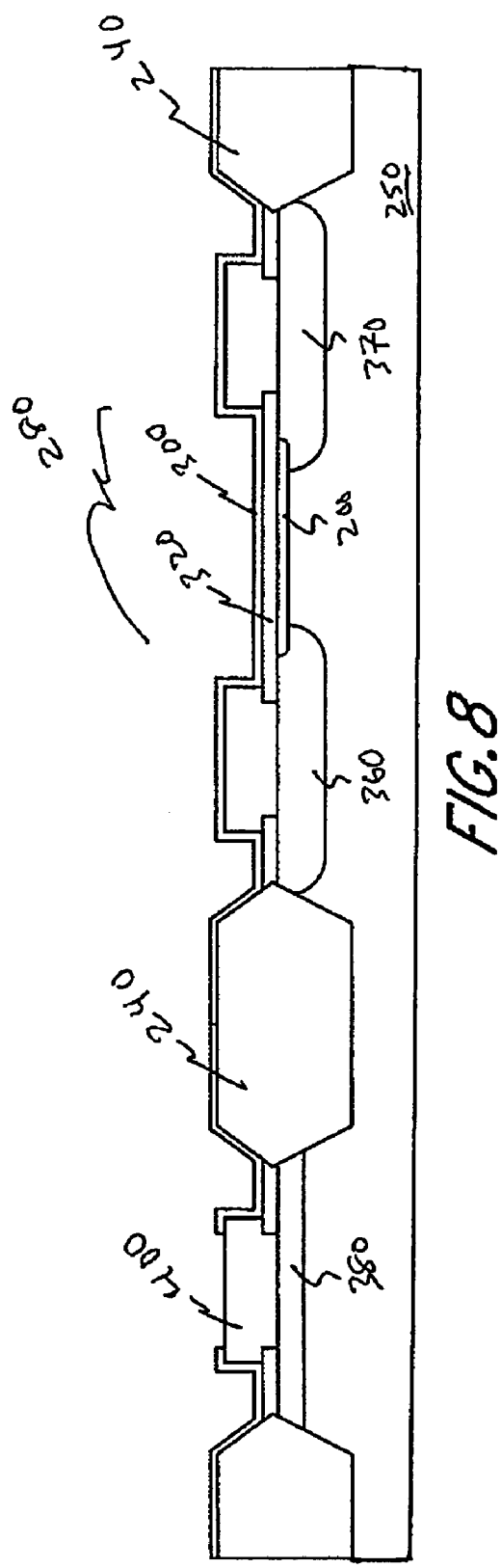

FIG. 8. FIG. 8 is a schematic cross section of a field effect transistor (FET) with a "naked" gate dielectric. Other materials besides poly-Si may be used for the gate, and a gate may be formed in the absence of separate conducting or semiconducting gate materials, as illustrated here. A transistor with just a nitride gate dielectric layer is an attractive embodiment of such a sensor. In this case, recognition elements are attached to the gate dielectric to form the target identification features on the gate. Additional processing of the gate region may occur depending upon the type of recognition elements attached and the nature of the targets and samples of interest.

Figure 9:
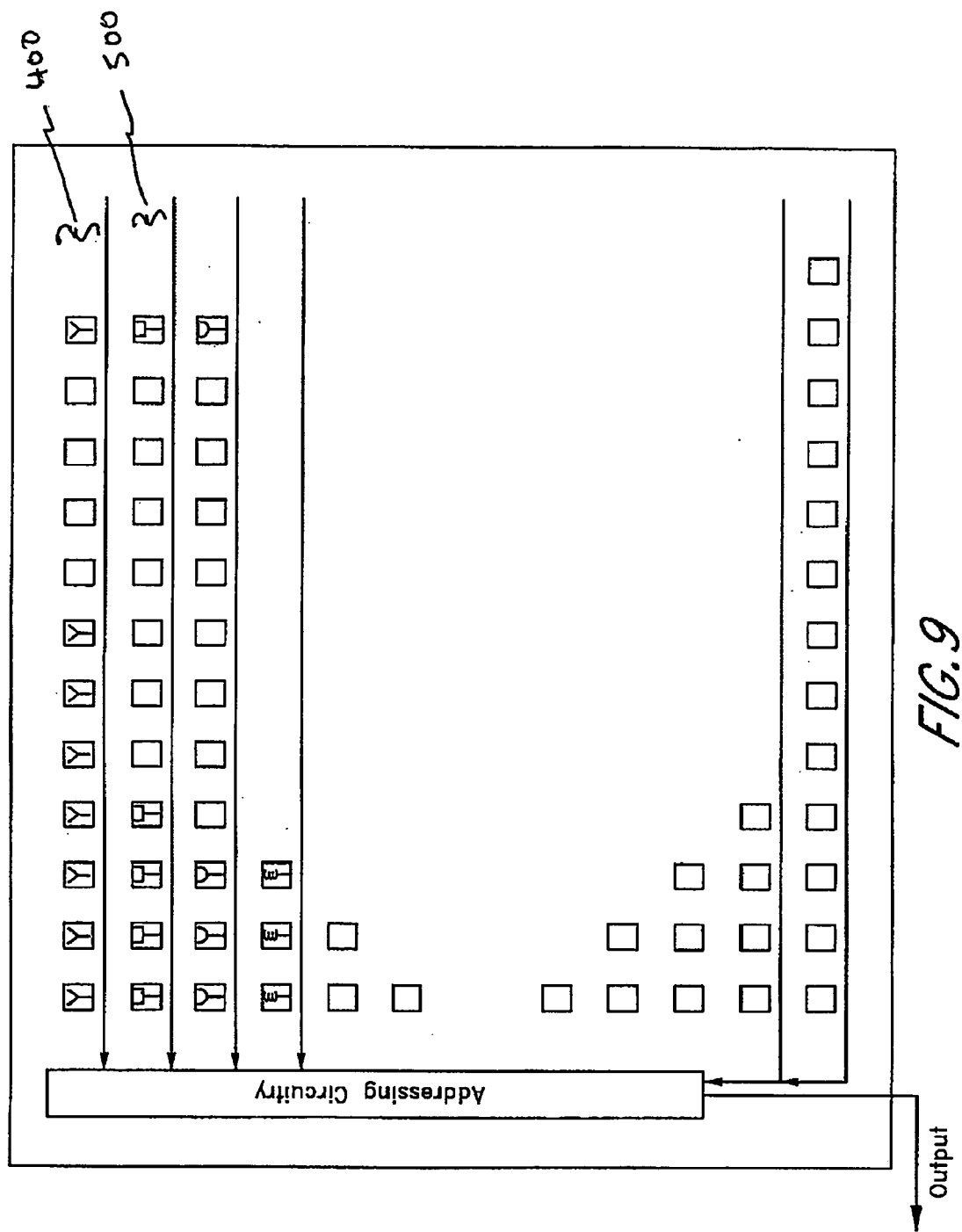

FIG. 9. FIG. 9 schematically illustrates a biosensor array. The array comprises rows and columns of biosensors, each sensor in turn comprising recognition elements for a particular target. Redundancy is provided by all sensors in each row having the same type of recognition element. Orthogonal recognition elements to the same target are present in different rows in this example. For large sensor arrays, a single row may have redundancy and orthogonal sensors as well as recognition elements for multiple different targets. In this example, the sensors are electronic devices integrated with addressing and information output circuitry. Typically the sensor output is an analog output indicating target detection, identification and concentration. Memory devices (not shown) and logic circuitry (not shown) together with readout circuitry (not shown) and other circuitry may be integrated on the same substrate or connected through hybrid means. Circuitry may be employed to convert an analog output signal to another electronic signal, such as a digital signal.

Figure 10:
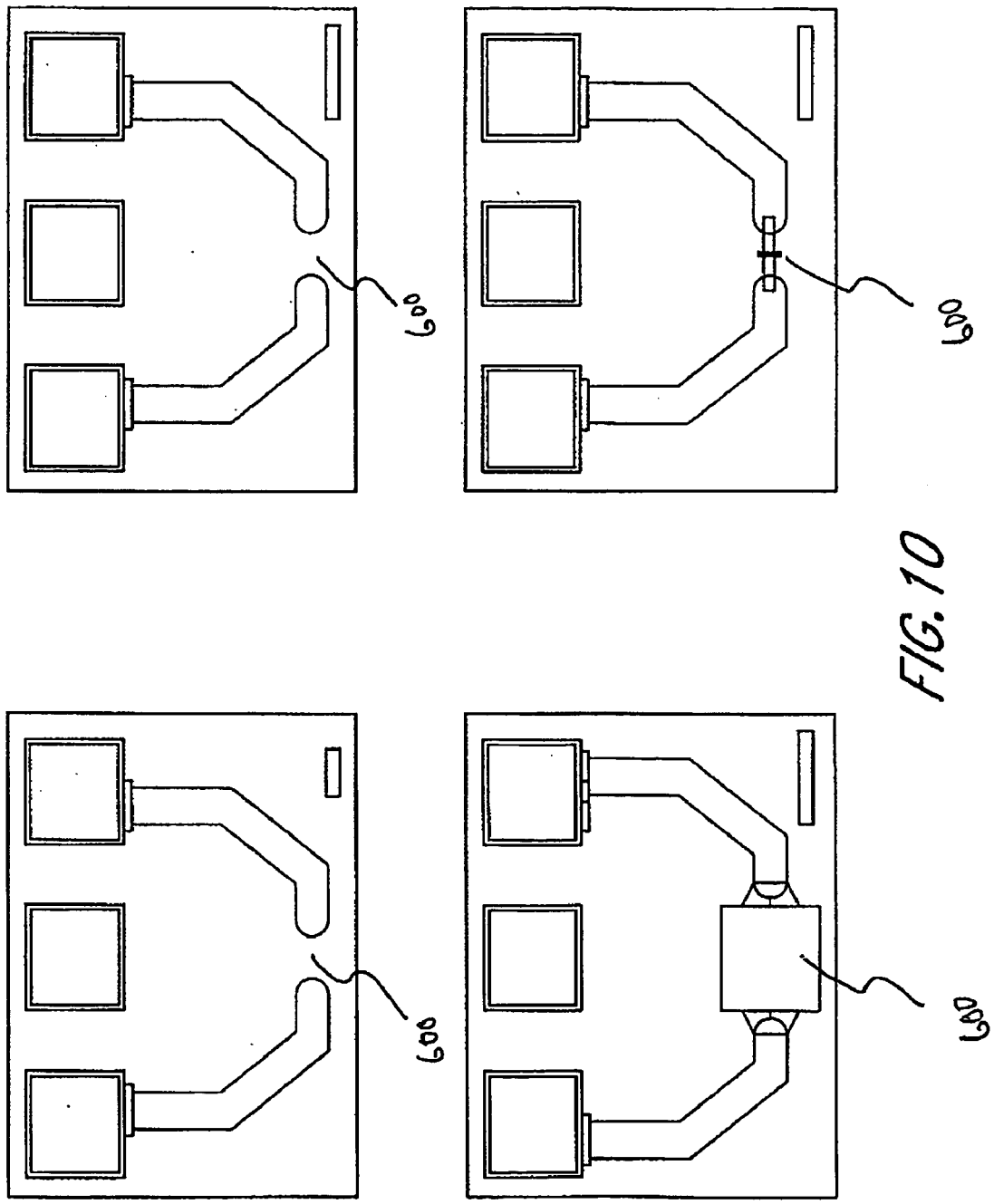

FIG. 10. FIG. 10 provides a top view representation of a possible sensor layout. A top view of four different sensors with different geometrical features is shown. The active sensor regions are in the lower central portion of each quad. An array here would constitute an array of either component members of the chip shown, or an array of the group shown, thereby comprising an array of groups of sensors. Such sensor group array components may comprise sensor configurations which vary according to the sensor objectives, sensitivity issues, recognition element binding issues or other desirable features.

FIGS. 11-25. FIGS. 11-25 are a series of cross sections illustrating the formation of a field effect transistor.

Figure 26:
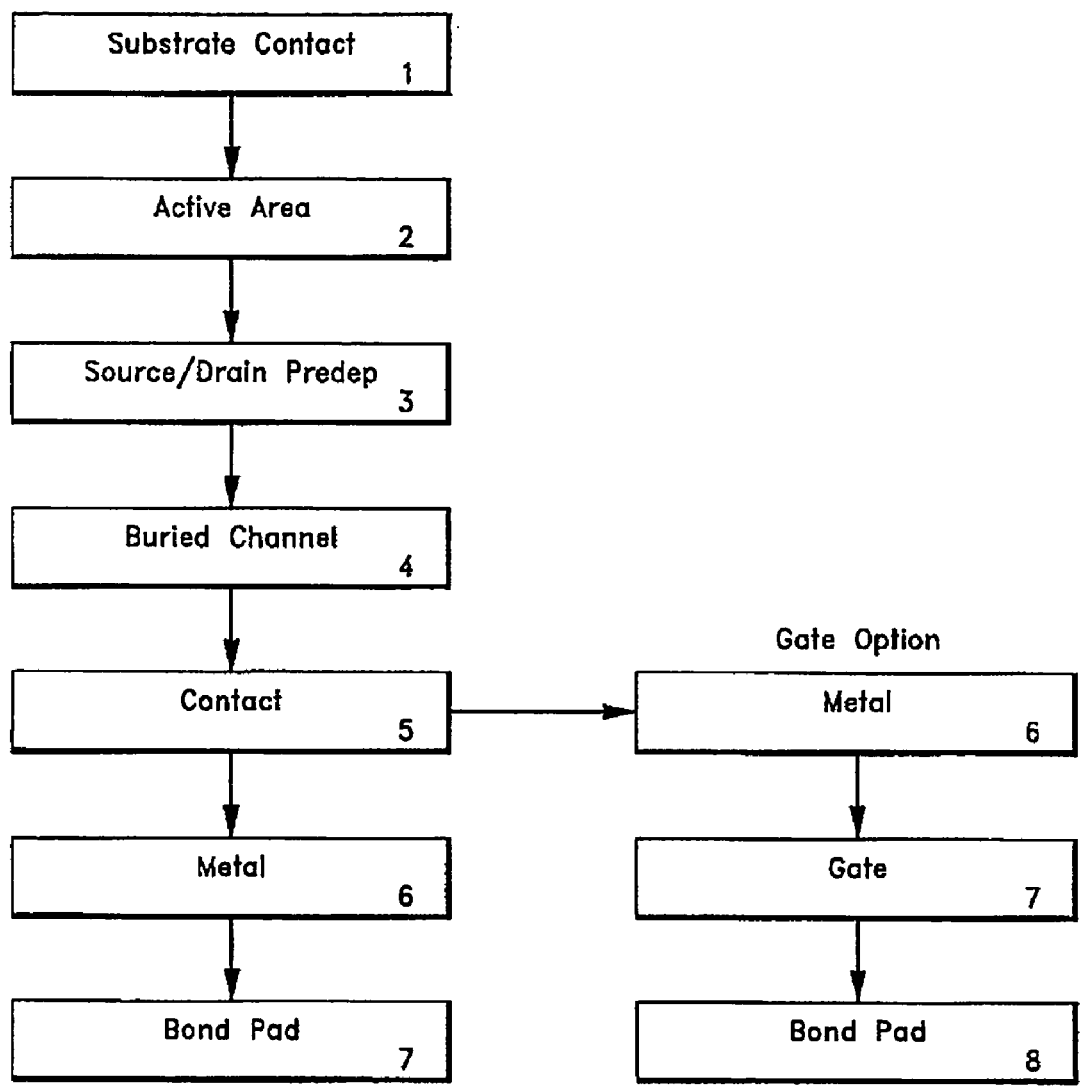

FIG. 26. FIG. 26 is a flow chart summarizing a set of process steps in forming a field effect transistor. Other process steps and materials will be apparent to the skilled artisan on reading this specification. For example, CMOS processes may be used.

Figure 27A:
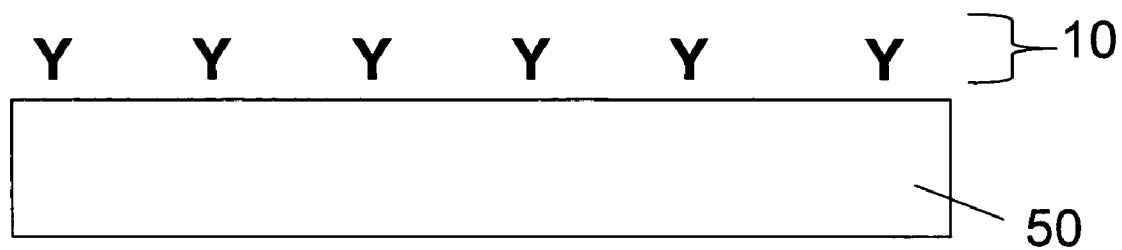
Figure 27B:
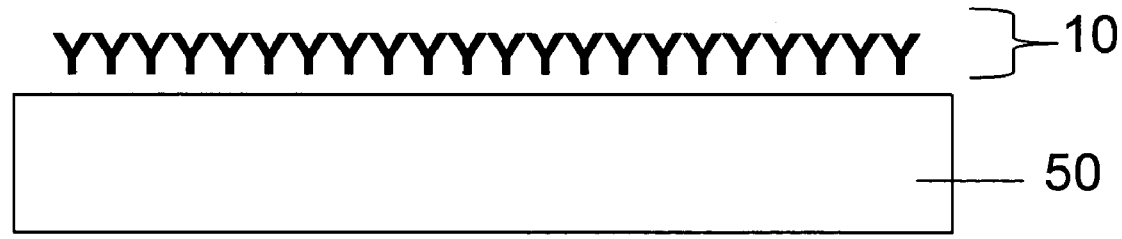

FIG. 27. A sensor recognition element group attached to a sensor gate region active area is illustrated for two recognition element surface densities (number of recognition elements per square micron). In FIG. 27A, the lower recognition element surface concentration (N1) when saturated with its specific target provides a signal $S_1$. The higher recognition element surface concentration for an active gate region of the same area illustrated in FIG. 27B provides a larger sensor output signal $S_2$. The higher the recognition element surface concentration for any particular sensor active gate area, the larger the influence on the sensor output signal and the larger the output signal when the recognition elements are fully bound or saturated. Thus, by increasing the receptor density, the sensitivity of the sensor is increased.

Figure 28:
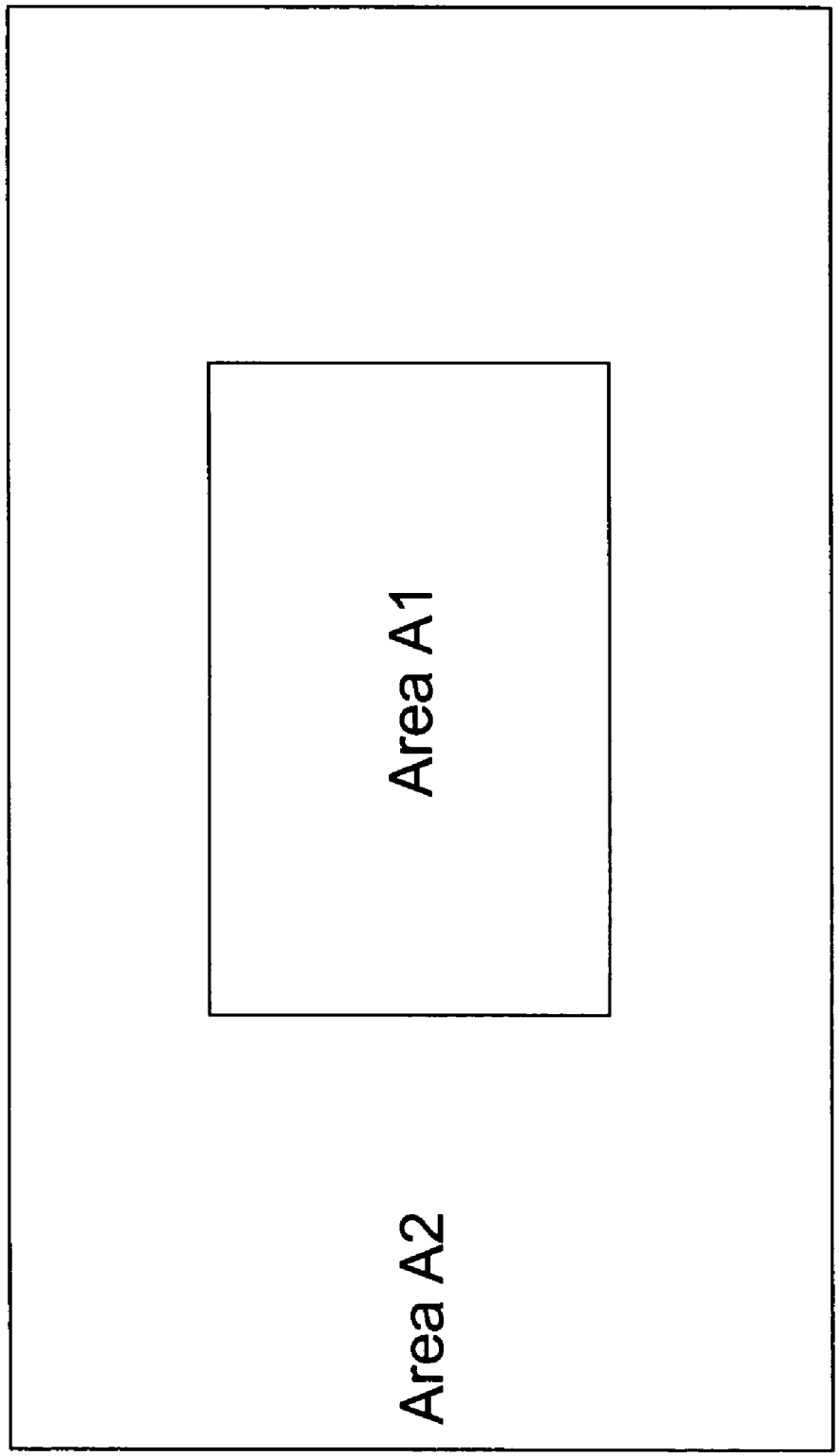

FIG. 28. Two sensor active gate areas are schematically represented with different active regions $A_1$ and $A_2$ comprising target recognition elements. For sensors of otherwise similar geometries, the smaller the active sensor area for a given recognition element surface density, the fewer recognition elements which need to be attached to the active gate area to obtain a measurable signal. Here, the width to length (W/L) ratio is identical for the two gates and thus the electrical characteristics will be identical. However the sensor with recognition element area $A_1$ uses significantly fewer recognition element components for the same sensor output signal, assuming saturation of recognition elements with the target. Thus, a sensor with a smaller active area is more sensitive than a sensor with a larger active area.

Figure 29:
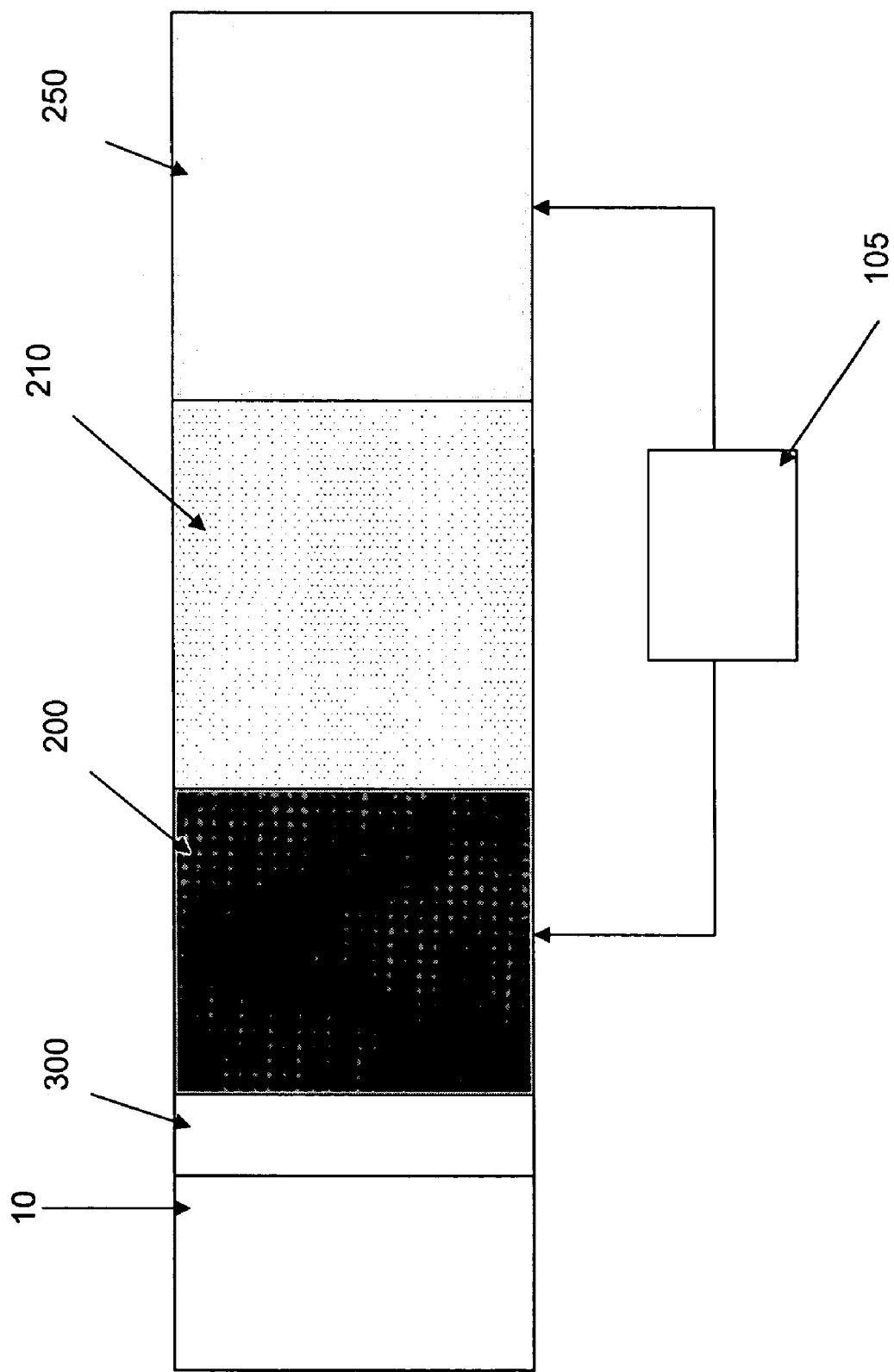

FIG. 29. FIG. 29 is a schematic representation of a buried p-channel sensor showing depletion isolation of the channel and the underlying n-type substrate. Here a reverse bias applied between the conducting channel and the underlying substrate increases or decreases the depletion region and encroaches on the conducting channel thereby affecting sensor sensitivity to recognition element bound targets. As discussed below, the reverse bias can be utilized to increase receptor sensitivity (% channel conductance change for a given amount of target attachment) and can be a used as a sensor output measure.

Figure 30:
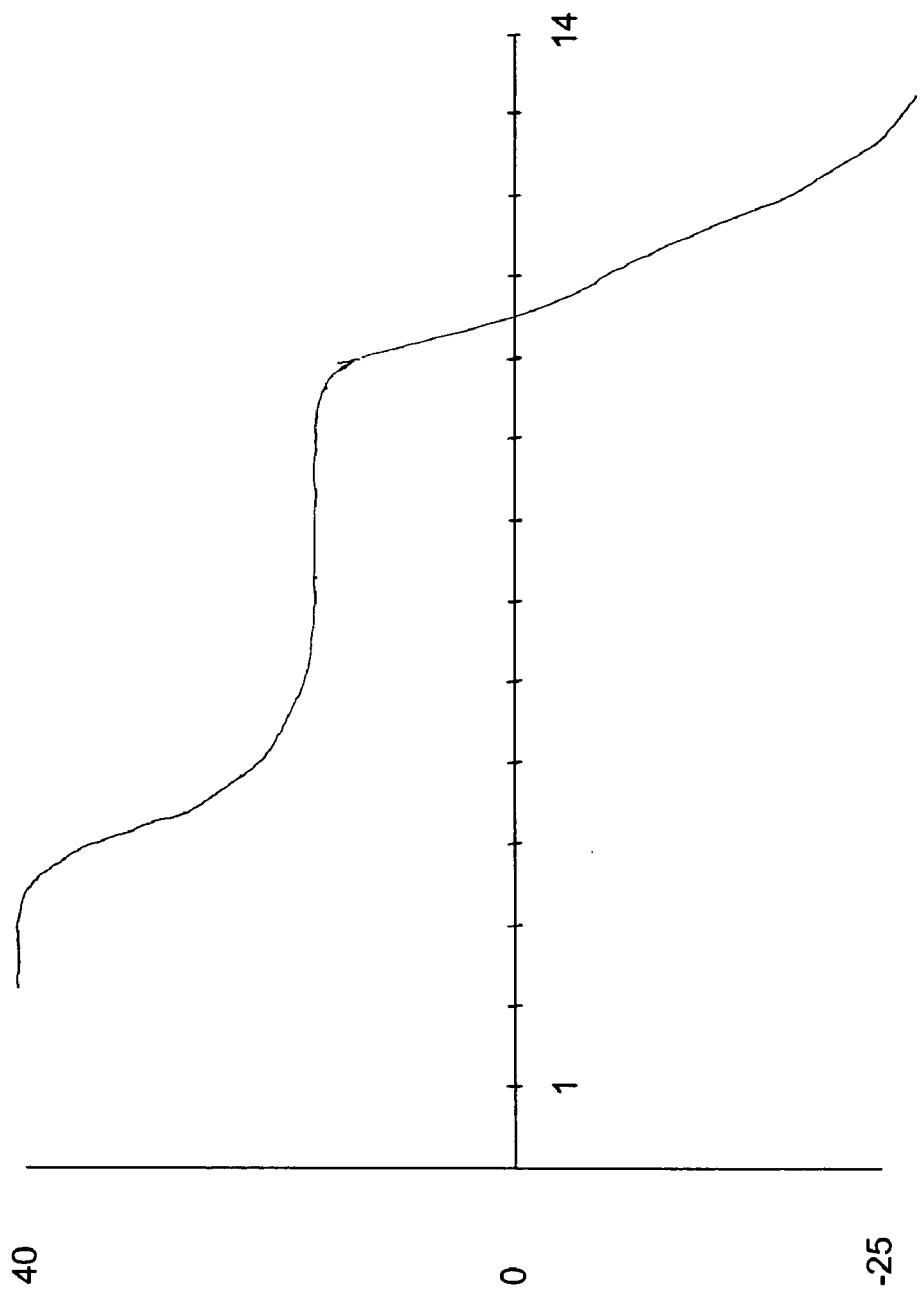

FIG. 30. Steptavidin associated net charge per molecule as influenced by pH is shown.

Figure 31:
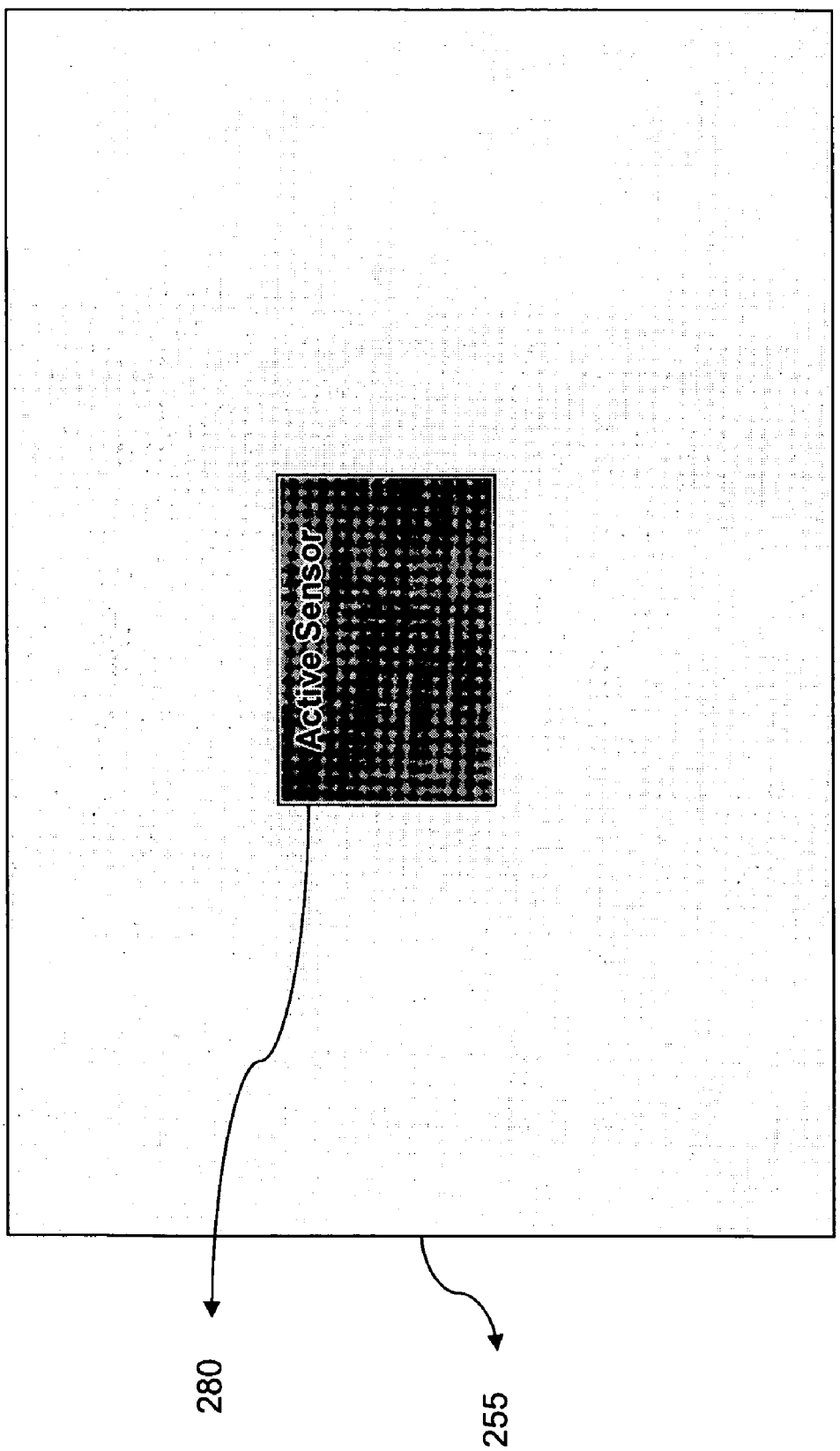

FIG. 31. The active region of a sensor with recognition elements and the surrounding environment (e.g., remainder of chip, package or substrate) is schematically represented. The surrounding region may be coated with a material to block recognition element binding and to prevent unwanted interactions, such as with moisture. The material may be, for example, a polymer displaying an inert surface such as parylene. Alternatively, the material may be a biochemical coating that does not bind to components in the sample. The biochemical coating may be a protein such as an antibody. The surrounding area is thus shielded from unwanted binding or other unwanted interactions.

Figure 32:
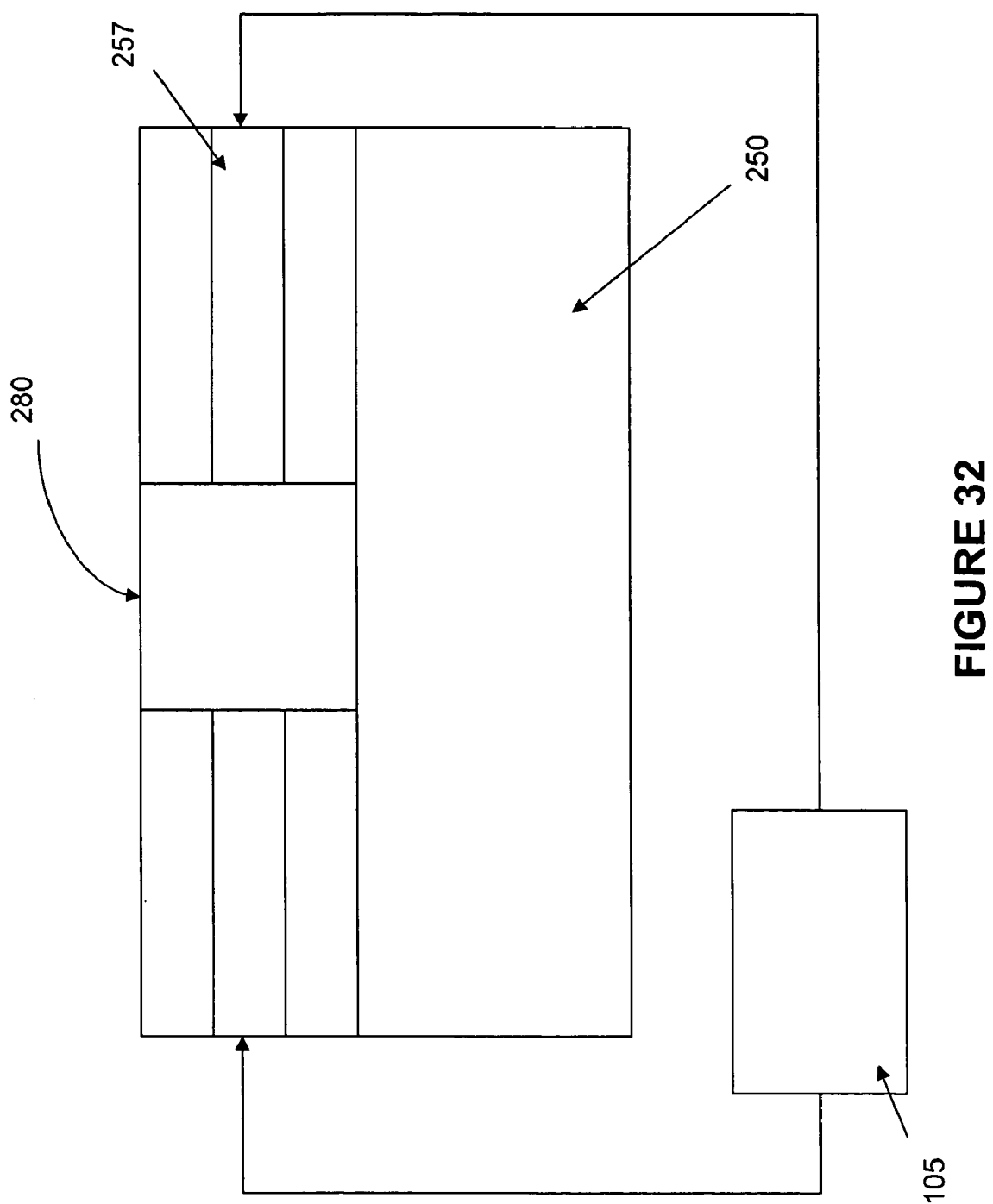

FIG. 32. A conducting shield is placed in the region surrounding the active sensor region and biased to prevent unwanted influence of attached molecules and materials in that region outside of the active sensor region. A voltage or ground may be supplied.

Figure 33:
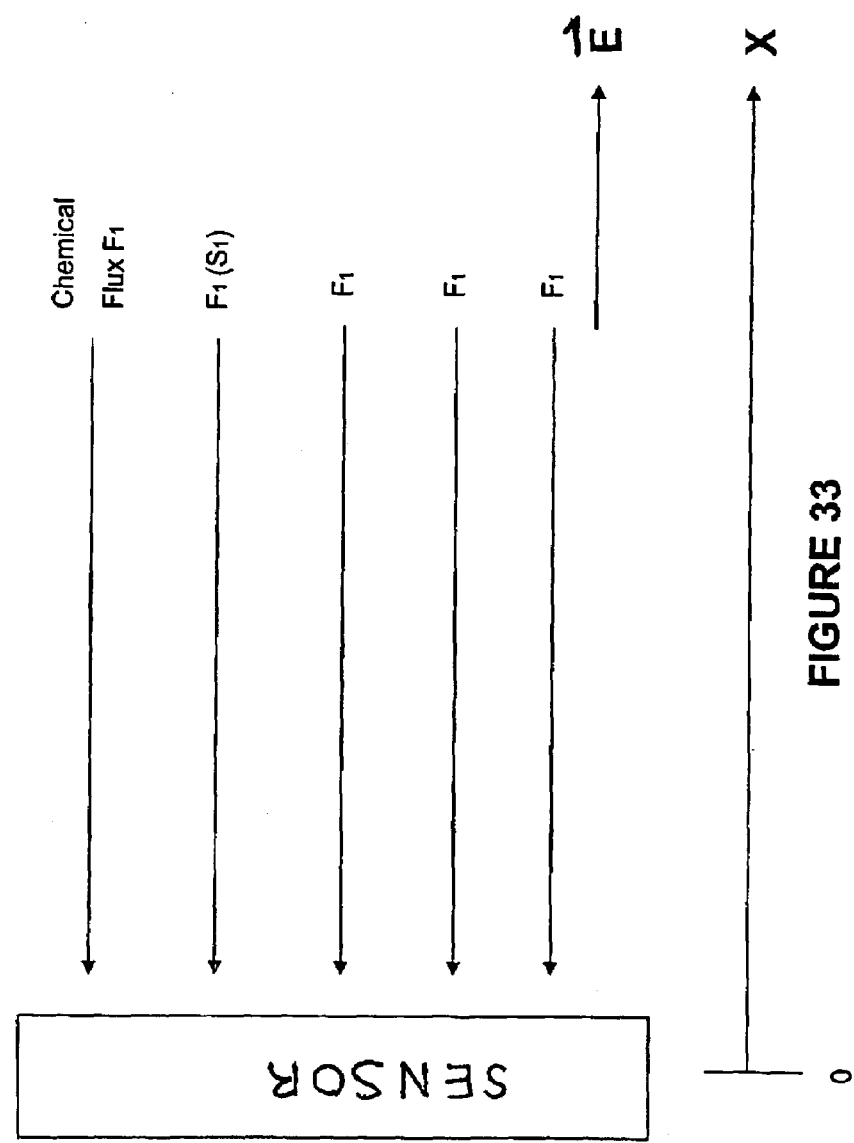

FIG. 33. A sensor with a bias voltage applied and the resultant electric field in the analyte region is schematically represented. FIG. 33 represents an electric filed (E) configuration as a function of location X. The concentration profile N1(X) for two electric field values (EI>>EII) and different surface concentrations C1I and C1II resulting from the two different electric field strengths.

Figure 34A:
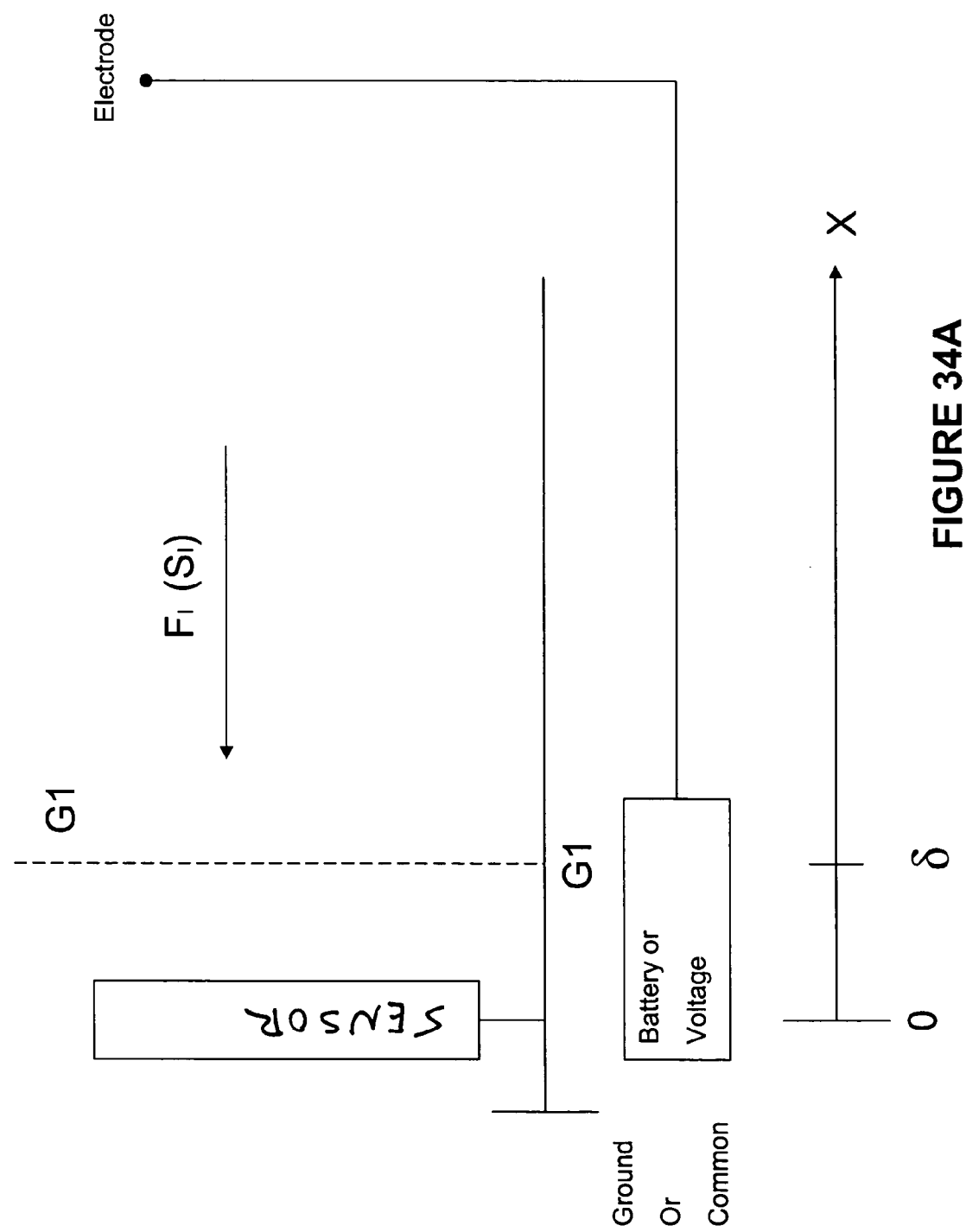
Figure 34B:
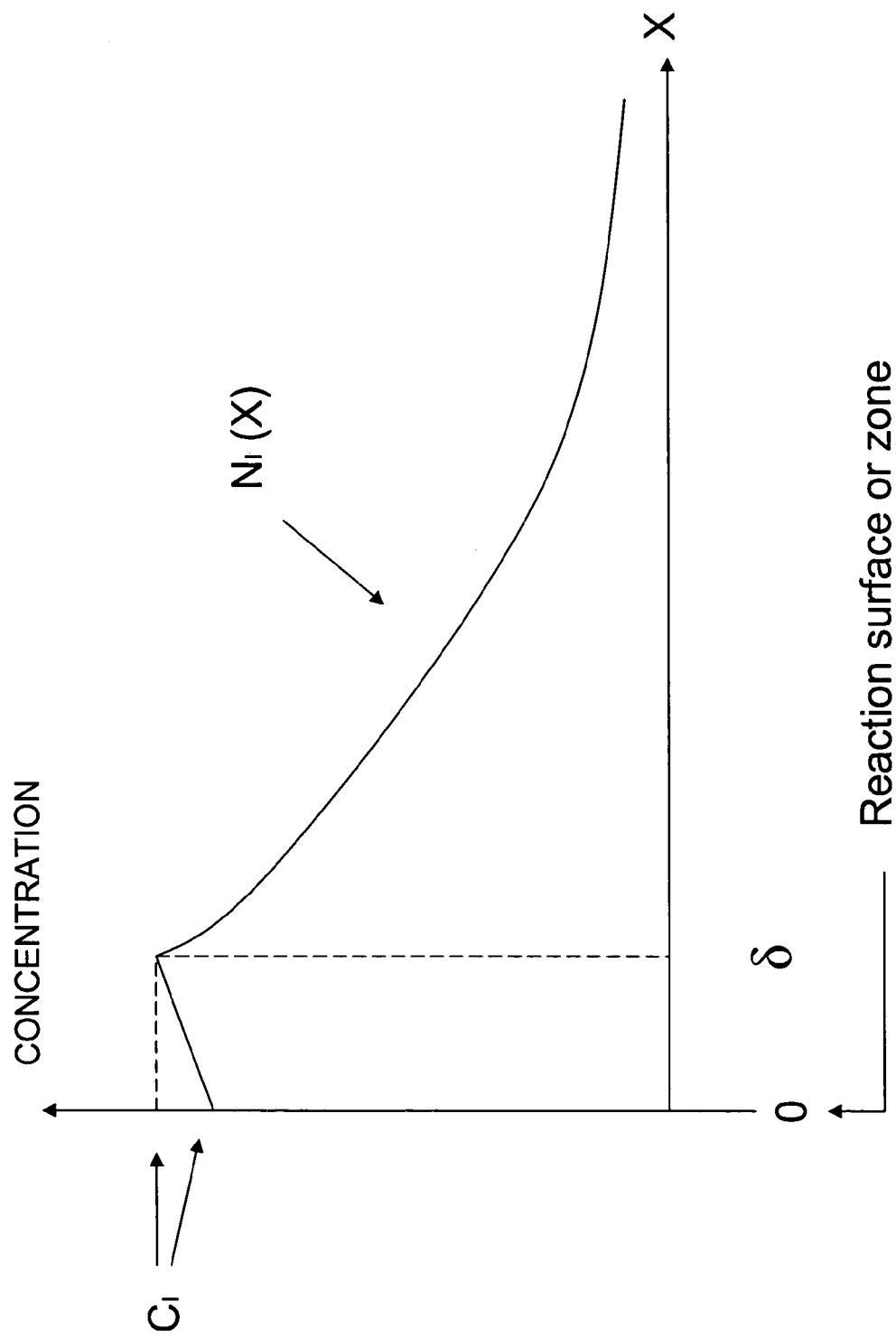

FIG. 34. FIG. 34A schematically illustrates a sensor and electrical grid placed in an active region biased with a voltage source, such as a battery. The sensor is connected to the grid G1 and both are grounded to one side of a battery. The other electrode (not shown) drops the battery voltage from that electrode to the grid G1. FIG. 34B shows the concentration N1(X) at the sensor surface, in the region between the grid and the sensor and between the grid and an electrode placed in the target environment.

Figure 35A:
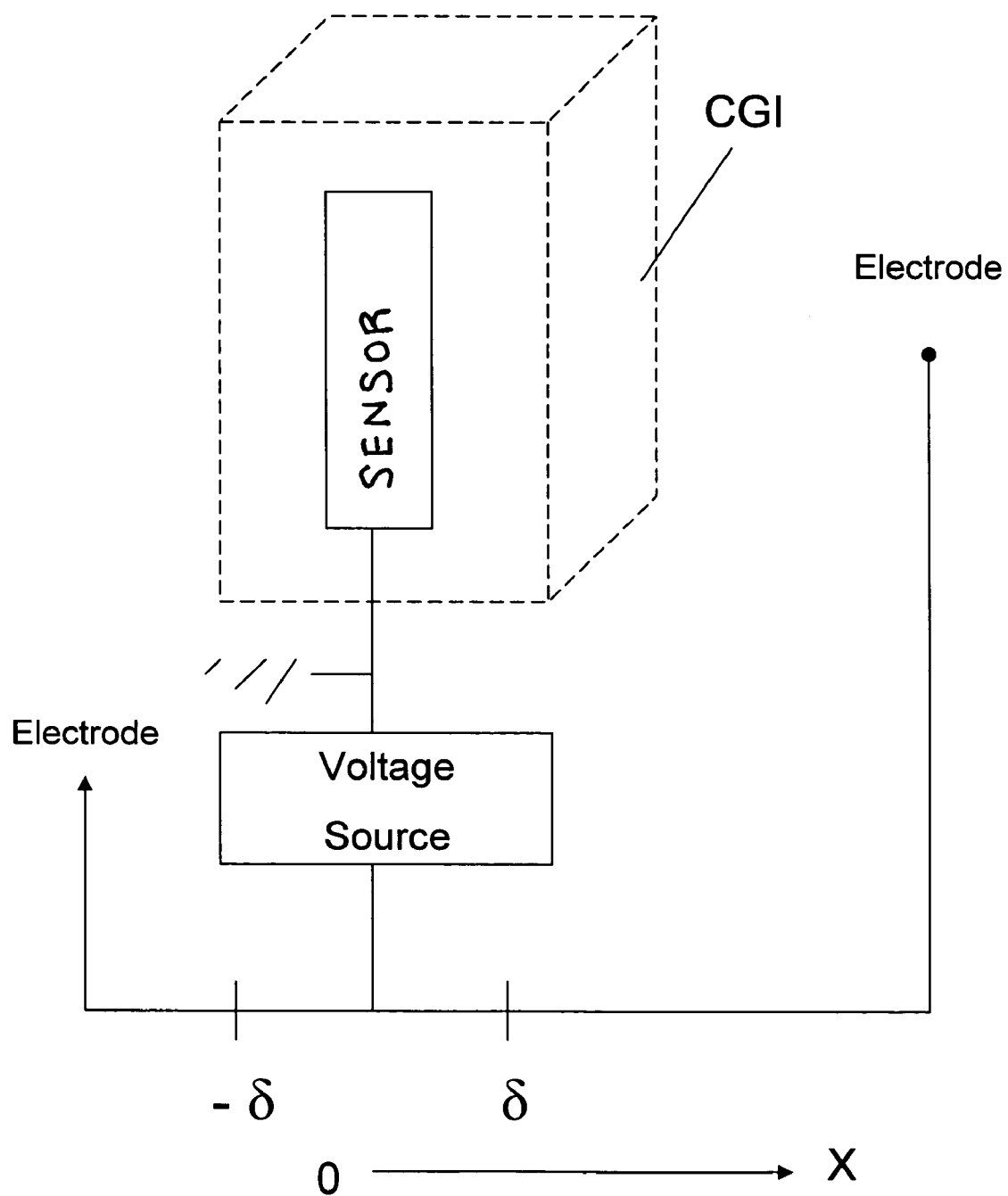
Figure 35B:
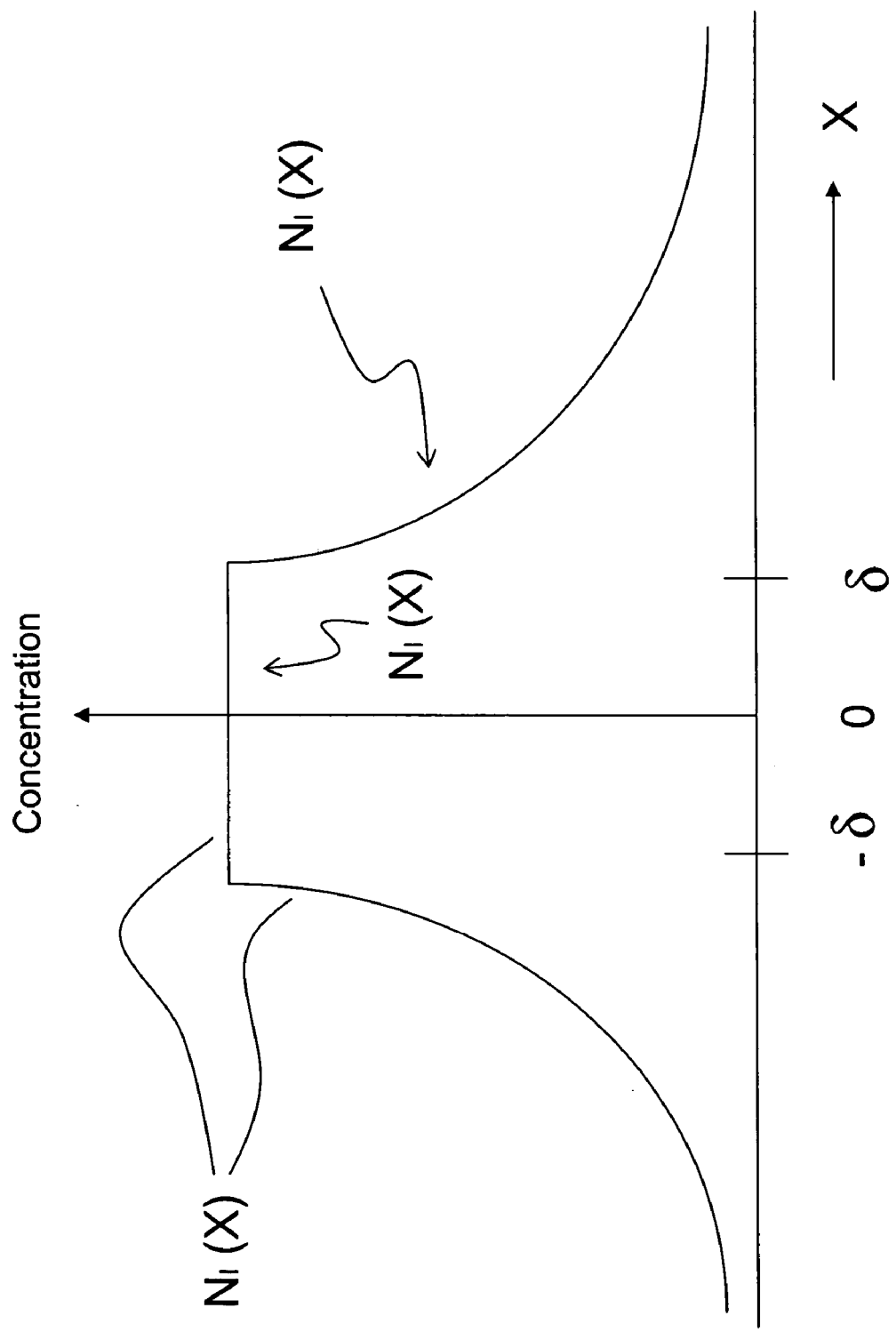

FIG. 35. A sensor for detecting a target species is placed in a 3 dimensional electrode cage (FIG. 35A). Both electrode cage and sensor are grounded. A battery biases an electrode in the collection region (electrode not shown). FIG. 35B illustrates the resulting concentration profile N1(X) of the target species S1 both inside and outside the cage.

Figure 36A:
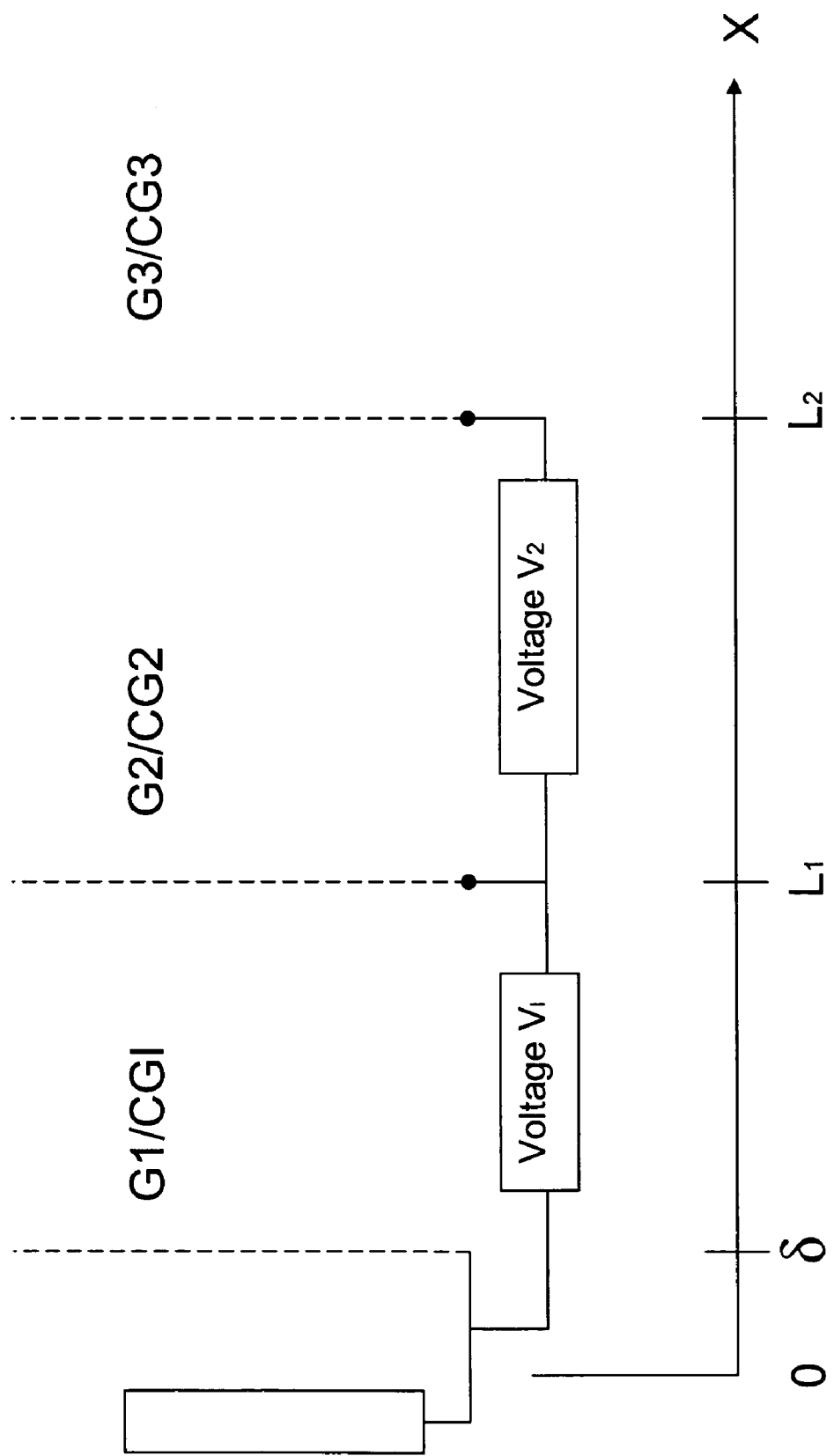
Figure 36B:
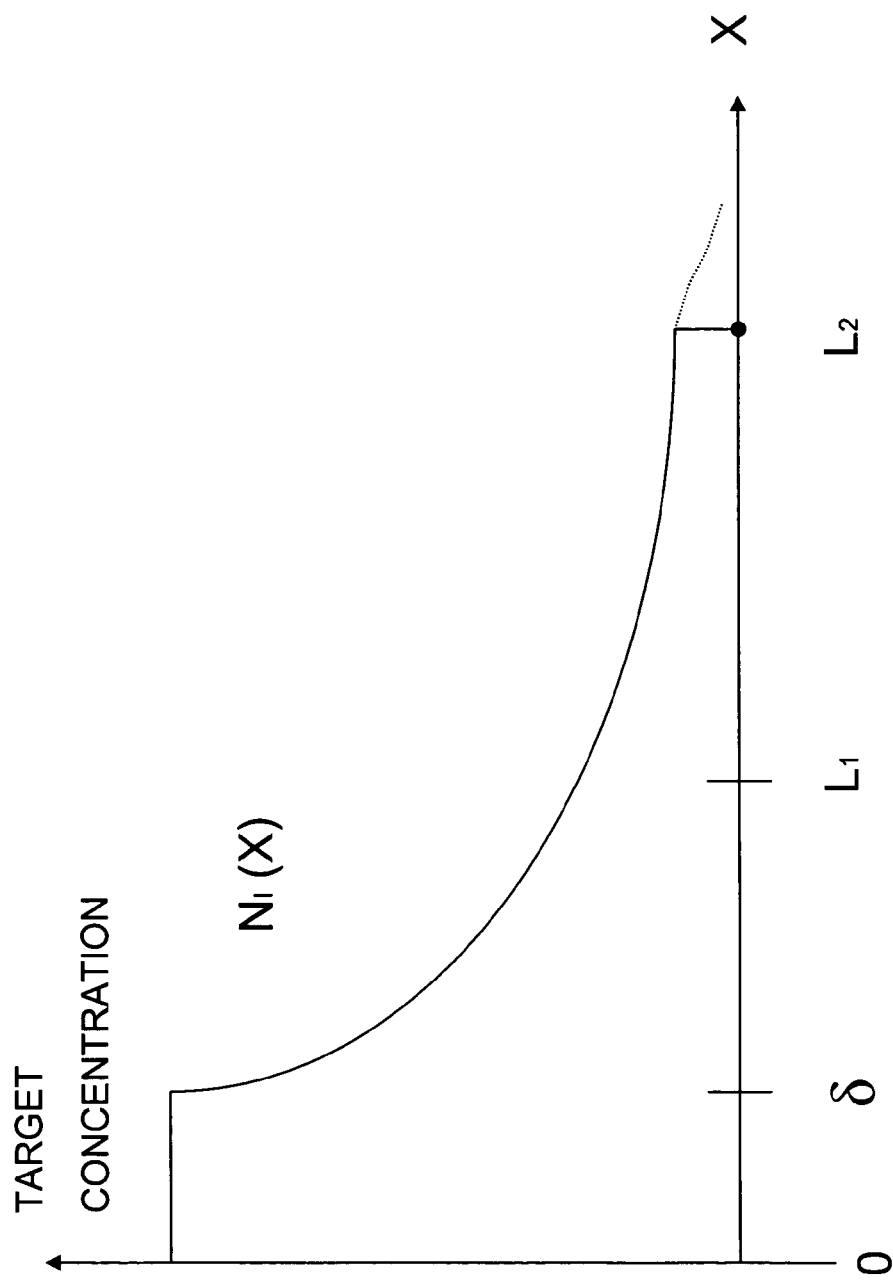

FIG. 36. A biochemical collection system is illustrated (FIG. 36A), comprising a sensor and three external electrodes, the first of which is located a distance delta from the sensor. The electrodes may be grids (G1, G2, G3), wires or cages (CG1, CG2, CG3). Electrode 2 (C2/CG2), located at L1, is biased at a first voltage with respect to the first electrode (C1/CG1). Electrode 3 (C3/CG3), located at L2, is biased at a second voltage with respect to electrode 2 (C2/CG2). Multiple collection zones are supported. Exemplary target S1 concentration profiles N1 (X) are represented in FIG. 36B for the different collection regions.

FIG. 37. A multiple electrode system active region comprises the gate dielectric over the channel region, such that the recognition element becomes the gate after binding.

"Recognition element" refers to any chemical, molecule or chemical system that is capable of interacting with a target molecule. Recognition elements can be, for example and without limitation, antibodies, antibody fragments, peptides, proteins, glycoproteins, enzymes, nucleic acids such as oligonucleotides, aptamers, DNA, cDNA and RNA, organic and inorganic molecules, sugars, polypeptides and other chemicals. In addition, a recognition element can be a thin film that is reactive with a target of interest.

The Sensor

Figure 1:
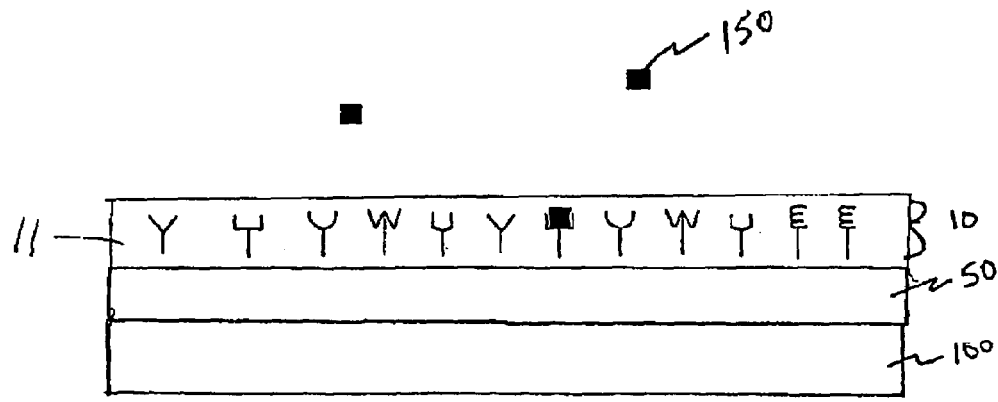
FIG. 1.

As illustrated in FIG. 1, the sensor comprises one or more recognition elements 10 attached to or in the vicinity of an active region 50 which is formed on an underlying solid support 100. Each recognition element is specific for a target of interest. The sensor is contacted with a sample and if the target of interest is present, binding of the target 150 to a recognition element 10 results in a sensor output signal. The type and magnitude of the signal will depend, in part, upon the charge associate with the target. Although generally described in terms of target binding, as discussed above, in some embodiments the action of the target on the receptor surface results in a sensor output signal.

In some embodiments the sensor comprises more than one type of recognition element 10. Each type of recognition element 10 is specific for a particular target. Multiple copies of each type of recognition element 10 are preferably attached to the active region 50 in order to produce a detectable signal upon binding. The number of recognition elements 10 necessary to produce a detectable signal will depend upon the nature of the target and can be readily determined by the skilled artisan.

Although two-dimensional arrangements of recognition elements in the active region are generally discussed herein, it is possible to have a three dimensional arrangement of recognition elements in the active area. For example, a gate material can be selected that allows for the dispersion of recognition elements throughout the material or the attachment of recognition elements to a three dimensional structure. In one embodiment the gate material is a material matrix 11 with recognition elements 10 dispersed throughout. In one embodiment the material matrix is a gel. In another embodiment the material matrix is a porous membrane with recognition elements attached throughout. In another embodiment, the active region is coated with a material, such as a gel, with recognition elements dispersed throughout the material. In other embodiments a three-dimensional arrangement of recognition elements is arrived at by linking recognition elements together, or by linking recognition elements to a scaffold or backbone that has been attached to the active area. For example, a chain of oligonucleotides, antibodies or other proteins or nucleic acids can be attached to the active area. In another embodiment recognition elements are linked to a porous membrane. Each of the recognition elements in a three dimensional arrangement can be specific for the same target or a variety of recognition elements that are specific for different targets can be used. In addition, each of the individual recognition elements can be identical or different.

The density of recognition elements 10 on the active area 50 is adjusted in order to produce a detectable signal if a target of interest is present in the sample. The density of recognition elements may also be increased in order to increase sensor sensitivity. In addition, the density and absolute number of recognition elements 10 on each sensor may be adjusted in order to provide additional information about the type and number of targets 150 present in a sample. For example, as described below, if approximately equal numbers of two or more types of recognition element are present, it is possible to determine both the presence and identity of one or more of the corresponding targets in the sample. On the other hand, the number of recognition elements 10 of each type can be adjusted such that the sensor can identify the number of targets 150 present.

For multiple target sensing, an output signal indicates that the sample has at least one target present. This may be useful, for example, in blood bank monitoring where the presence of any one of a large number of diseases indicates that the blood is not suitable for use in transfusions.

Figure 2:
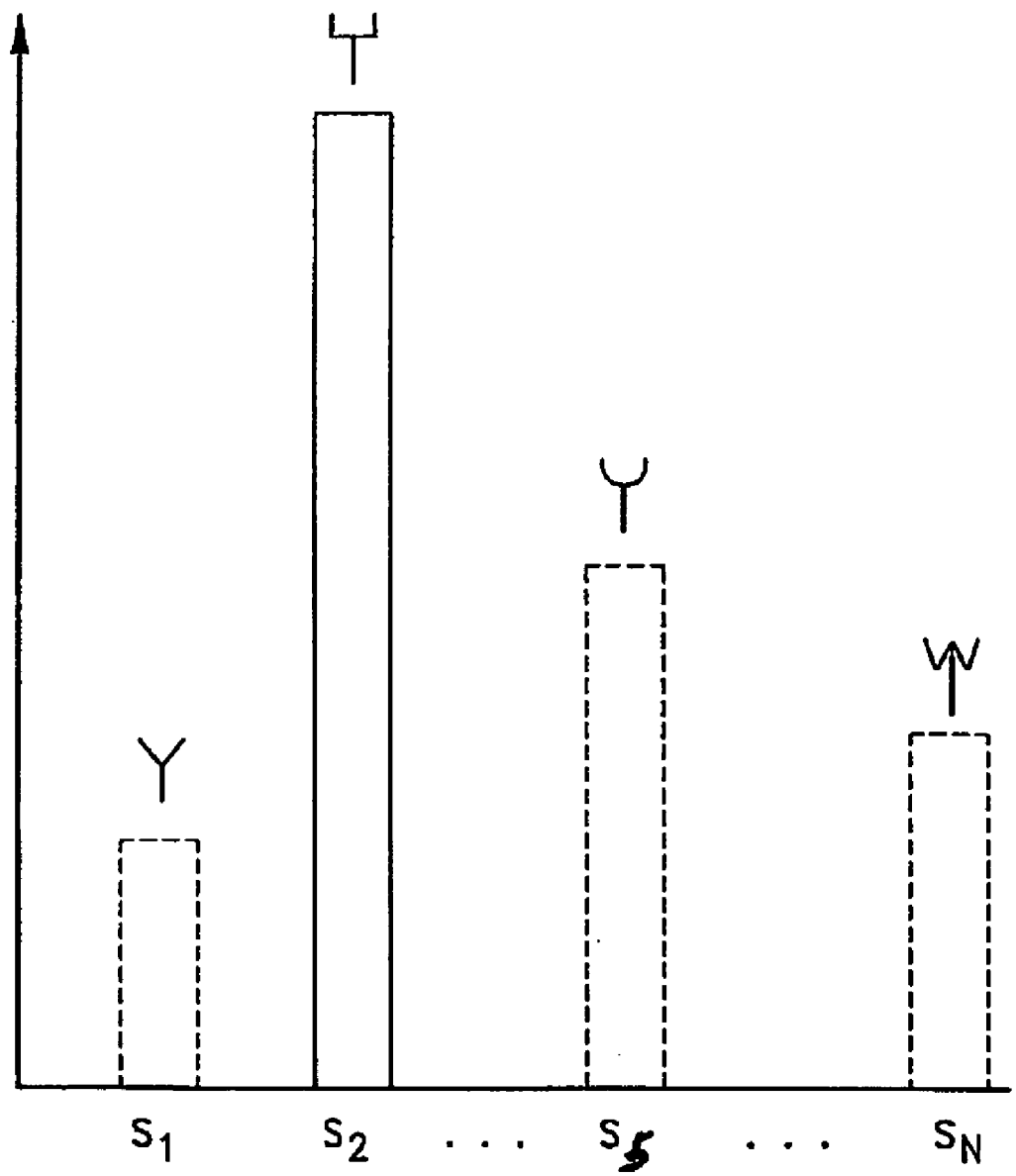
FIG. 2.

In a particular embodiment, the total number of each type of recognition element on a given sensor is approximately equal. That is, the surface density (number/square micron) of recognition elements specific for each target is approximately equal. In addition the surface density of recognition elements for each target type is preferably high enough to produce a detectable signal but low enough that the recognition elements are readily saturated by a sample containing that target type. The magnitude of the output signal produced by binding of each target will depend on the recognition element and target properties, including the charge and/or the chemical potential associated with the bound target. Because of the equal surface density of each type of recognition element, differences in the amplitude of the measured signal are attributable to the identity of the target and not to differences in the number of recognition element molecules bound. The type of signal expected for each target can be predetermined by exposing the sensor to one target at a time in a calibration process. As a result, the distinct signal produced by binding of each target allows for the determination of the identity of a particular target in the sample (FIG. 2). In addition, if more than one target is present, the combined output signal is parsed to determine the identity of more than one target.

Figure 3:
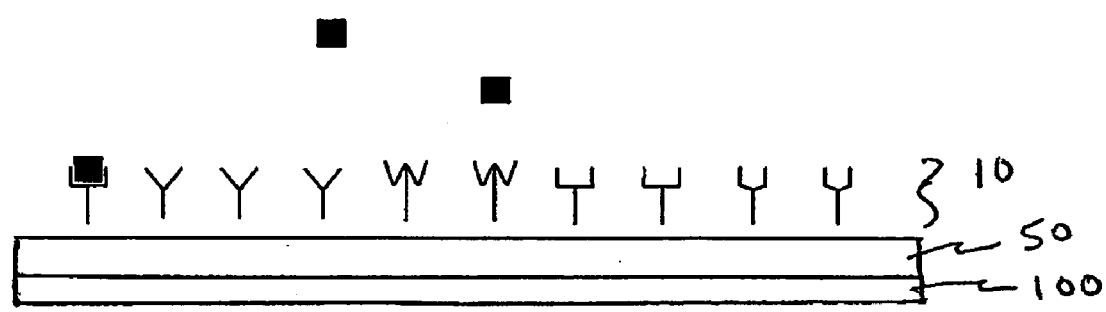
FIG. 3.
Figure 4:
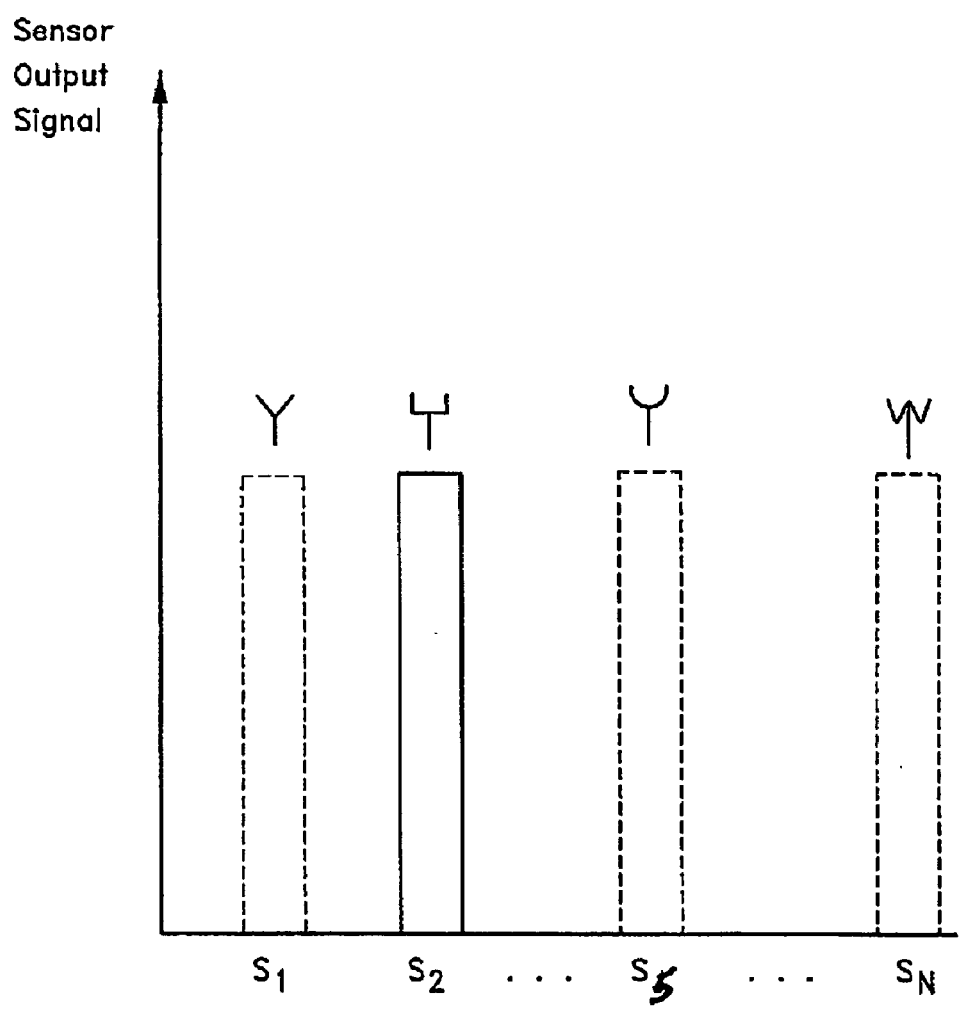
FIG. 4.
Figure 5:
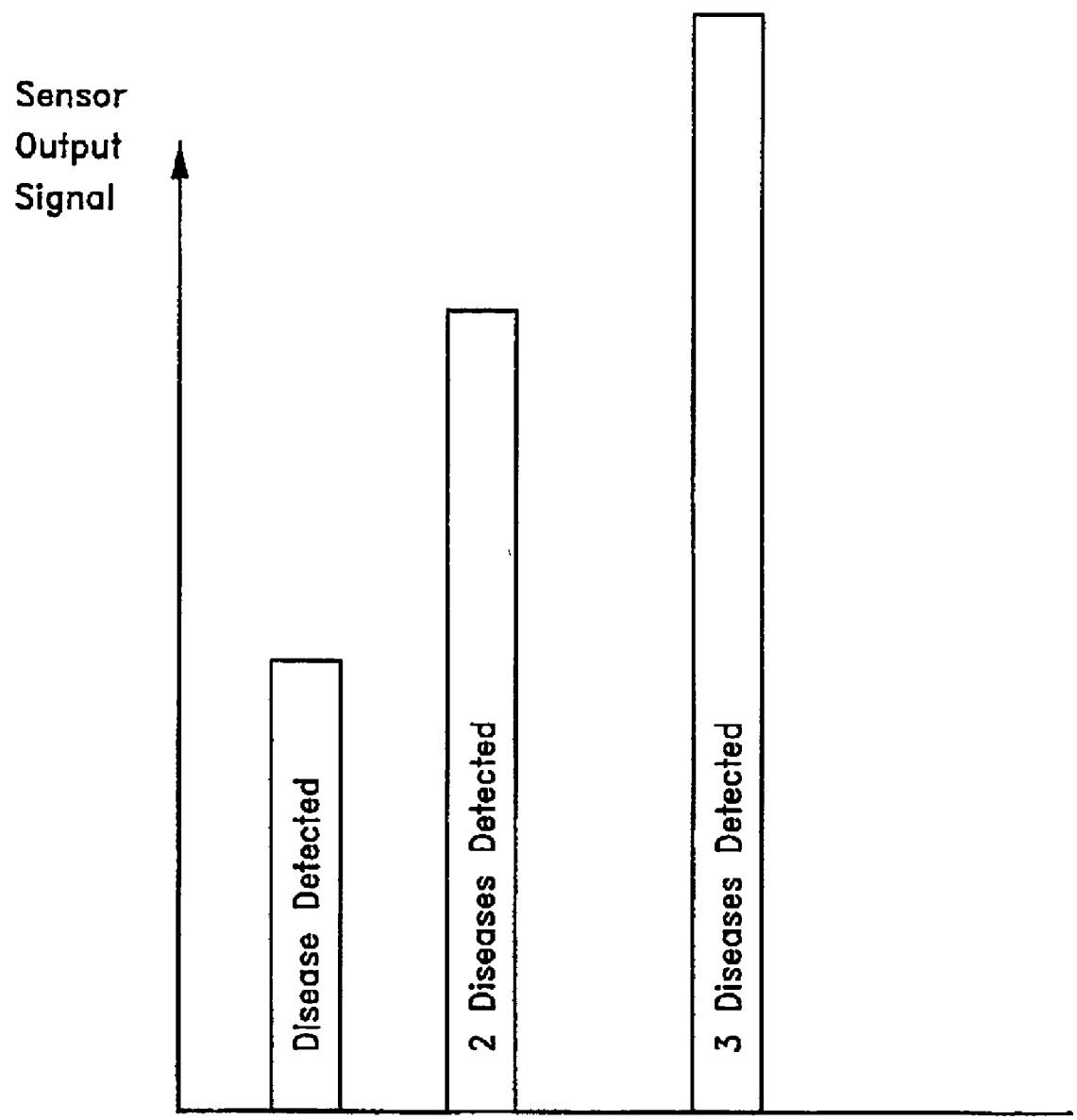
FIG. 5.

In another embodiment, the density and absolute number of each type of recognition element is not equal (FIG. 3). Preferably, the number of each type of recognition element is selected such that the resultant signal for binding of any of the targets is of approximately the same magnitude, regardless of the identity of the target. FIG. 4 illustrates this embodiment, in which binding of each type of target to its particular recognition elements produces an identical signal. The total number of different types of targets present can then be determined based on the total amplitude of the signal. For example, if two types of targets are present a signal would be measured that is twice as large as if a single type of target is present. In this way, it can be determined how many of the types of targets being tested for are present in the sample. This type of sensor configuration has utility, for example, in disease diagnostics, where the number of diseases a physician should be concerned with can be readily determined. This example is illustrated in FIG. 5, where each target is an indicator of a different disease. Here, a signal of particular amplitude (far left bar) indicates the presence of one type of target, corresponding to one disease. A signal that is of twice the magnitude (middle bar) is indicative of two diseases and a signal that is three times larger (far right bar) is indicative of three diseases.

Figure 6:
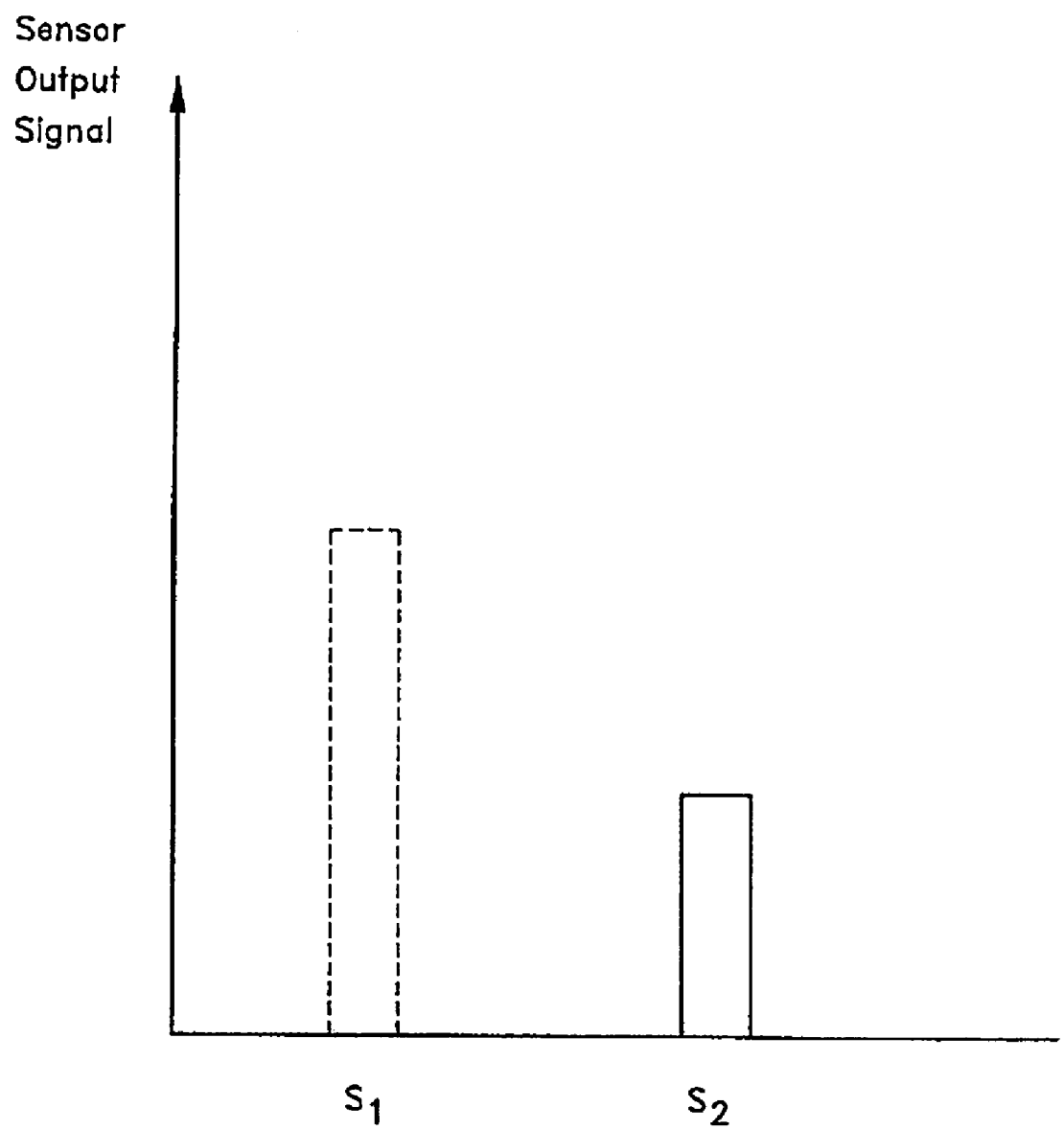
FIG. 6.

In some situations, the amount of target present in a sample may not be sufficient to saturate all of the recognition elements. In this case, as illustrated in FIG. 6, the magnitude of the signal produced by target binding may be less (solid line) than the expected signal (broken line). A control sample, comprising a known concentration of target, can be used to determine the expected signal for each sensor through routine experimentation.

By using samples of different dilutions and measuring signal output, detailed information on the kinetics of the binding reaction can be determined. For example, the binding constant of the target can be determined.

In addition, a signal that is less than expected may provide additional information about the target or about conditions related to the presence of a target. For example, if a sensor is used to diagnose the presence of a disease, a smaller than expected signal from a disease related antigen may indicate that the disease is at an early stage. Thus, the sensor can be utilized to determine the stage of a disease in addition to simply diagnosing the disease. In other embodiments the sensor is used to determine viral load in a patient.

In one embodiment the sensor comprises orthogonal recognition elements. Here, "orthogonal" refers to two or more recognition elements that are specific for the same target. Preferably, each of the recognition elements recognizes a different portion of the target. For example, the sensor may comprise two or more antibodies to a particular antigen, such as botulinum toxin. When two or more antibodies are used, each antibody preferably binds to a different epitope on the target antigen. In another specific embodiment two or more different oligonucleotides are provided that bind to the same target. For example, two different oligos may bind to different parts of the same DNA or RNA strand. The use of orthogonal recognition elements provides additional redundancy and helps avoid false positives and false negatives that may occur if only a single recognition element type is used for a particular target.

In some embodiments, the sensor operates as a switch. In these embodiments the number and density of recognition elements is selected such that the production of any measurable signal (or elimination of any signal) corresponds to a particular concentration of a target in the sample. That is, when a minimum concentration of a target is present, the sensor "turns on" or "turns off." In this way the presence of a minimum concentration of target in a sample can be determined. This may be useful, for example, in determining if an environmental sample comprises a minimum level of a toxin. In these embodiments, the channel, as described below, is preferably not conducting in the absence of target binding to the active region.

Figure 7:
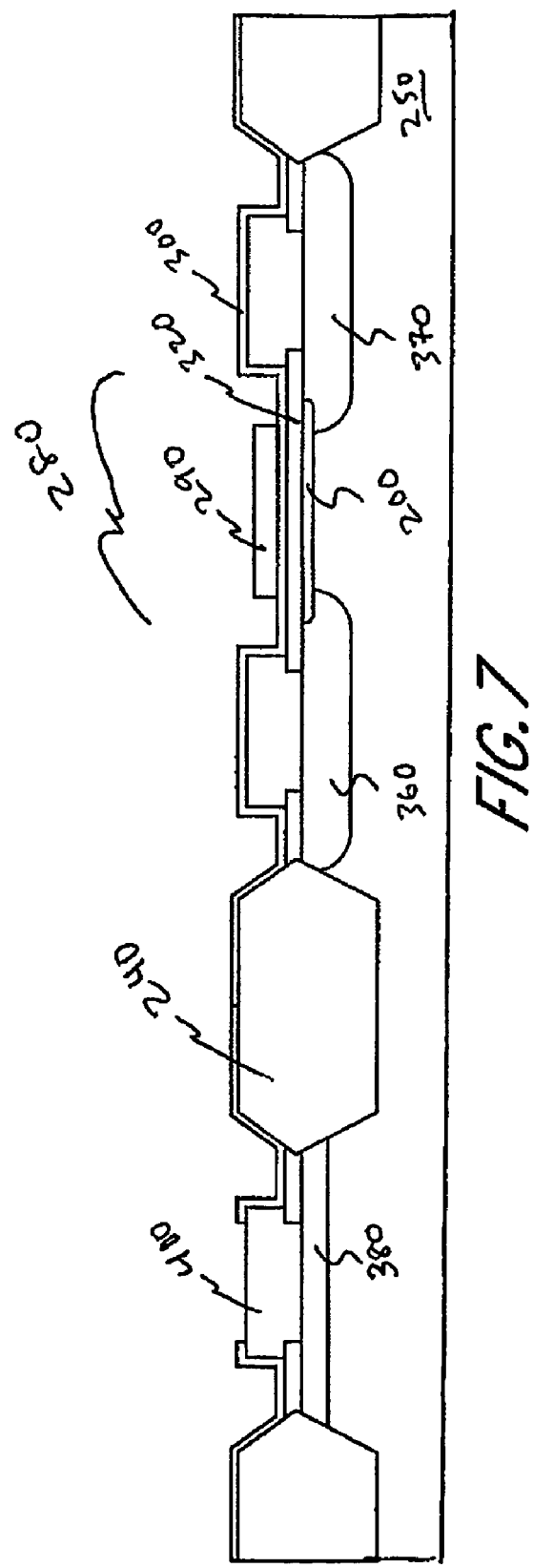
FIG. 7.

With reference to FIG. 7, in the preferred embodiments the sensor comprises a field effect transistor (FET) operating in accumulation mode. However, in some embodiments and with some targets the transistor will operate in depletion mode. When operating in depletion mode, the sensor will be able to detect gate changes unless the channel inverts to the type opposite the source and drain regions.

Recognition elements are bound to the gate region of the transistor. In one embodiment the recognition elements are bound to a gate electrode of poly-Si, as illustrated in FIG. 7. In other embodiments the gate material may be, for example, a polymer, a membrane, a protein layer or a biochemical layer. Other gate materials known in the art may be utilized.

In the illustrated embodiment, a buried conducting p-channel 200 is isolated from an n-substrate 250. The p channel conducts in the absence of any input from the top gate. The channel connects a source region 360 and a drain 370. The source and drain are preferably p+. In other embodiments the buried conducting channel is an n-channel. In these embodiments the source and drain are preferably n+.

The gate stack 280 of the illustrated embodiment comprises a polysilicon layer 290 over a gate dielectric, which comprises a layer of silicon nitride 300 over a layer of silicon oxide 320 in the illustrated embodiment. The gate dielectric is preferably thick enough to block unwanted sample effects, such as the effects of moisture. Preferably, the gate dielectric is between about 100 Å and about 5000 Å thick, more preferably between about 500 Å about 3500 Å thick, even more preferably about 3000 Å thick. In the illustrated embodiment gate dielectric is about 3000 Å thick. Other conductive materials besides polysilicon may be used for the top gate electrode. Recognition elements (not shown) are attached to the gate electrode or insulator to form the active region, as described in more detail below. In other embodiments a material that facilitates recognition element binding is deposited or formed over the gate electrode and the recognition elements are attached to this material. In still other embodiments a material matrix comprising recognition elements, such as a gel or porous membrane with recognition elements dispersed therethrough, is applied to the active region. In some embodiments a material that interacts with one or more particular targets is deposited or formed over the gate electrode or gate dielectric.

With reference to FIG. 8, in other embodiments a gate electrode is not present and the recognition elements are bound to the gate dielectric layer 300 to form the active region. In still other embodiments a material that facilitates recognition element binding is deposited over the gate dielectric layer 300 and the recognition elements are attached to this material. In further embodiments a material that contains recognition elements is placed over the gate dielectric layer 300.

The gate dielectric may also serve as a barrier material that protects the substrate, for example from deleterious interactions with the sample. As illustrated in FIGS. 7 and 8, the gate dielectric extends over and protects the rest of the transistor except at the external electrical contact openings. When it functions as a protective layer, the gate dielectric is preferably deposited to a thickness that is able to protect the sensor from a particular sample, as can be readily determined by the skilled artisan. In other embodiments the protective layer is a conductor or semiconductor or charged material, as described in more detail below. The protective layer preferably does not bind charged molecules in the sample and may actually repel charged molecules.

Figure 38:
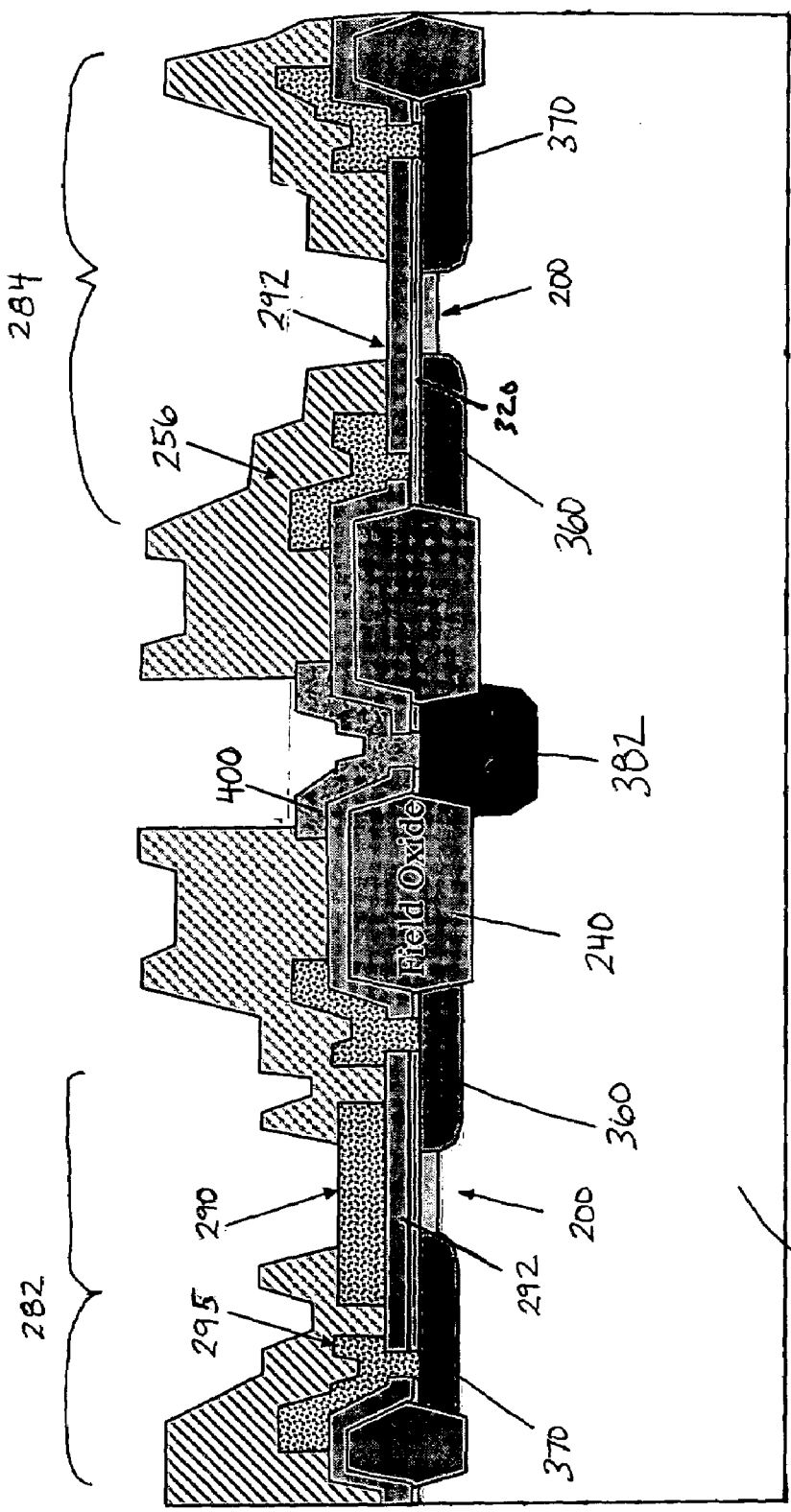

A cross section of two sensors formed in the same substrate is illustrated in FIG. 38. A first sensor 282 comprising a poly-Si gate 290 and a second sensor 284 comprising a nitride gate 292 are shown. The substrate 250 is a 10 ohm-cm n-type substrate. The source and drain interconnects 295 are also comprised of poly-Si in the illustrated embodiment, although other conducting materials may be used. An implanted p channel 200 is utilized in both sensors 282, 284. The implanted ion dose may be, for example, 1.0, 1.2, 1.4 or 1.6E12 (number/cm$^2$). A top nitride layer 256 overlaps the gate nitride 292 or poly-Si 290 to insure that no moisture or other chemical is able to leak to the oxide 320. In the illustrated embodiment the top nitride is about 2 µm thick. The thickness of the gate nitride is preferably selected to block moisture. In the illustrated embodiment the gate nitride is approximately 0.3 µm thick.

FIGS. 11 through 25 illustrate the formation of a FET including a buried p type channel for use in a sensor. These steps are summarized generally in FIG. 26. However, one of skill in the art will recognize that other conventional methods may be used to form the FET utilized in the sensor.

Figure 11:
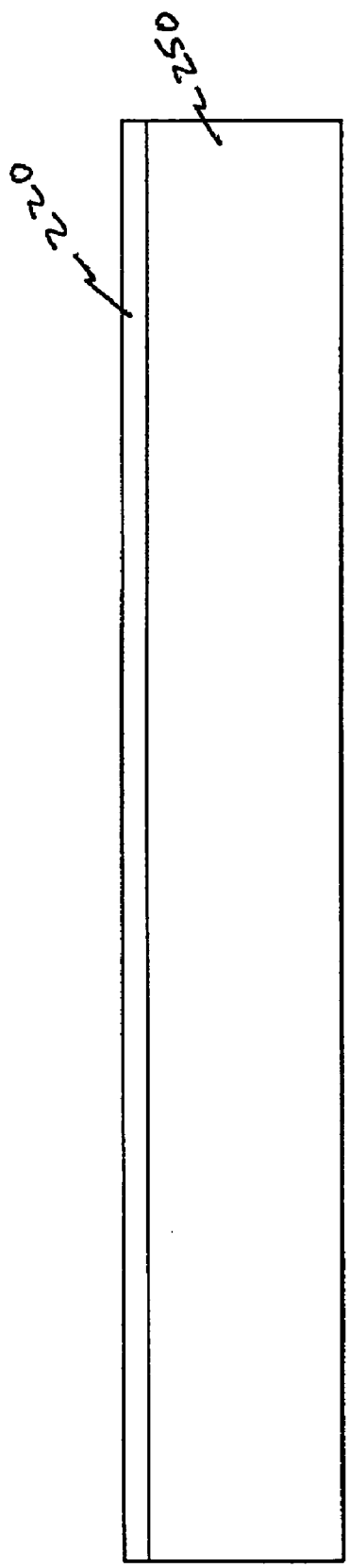
Figure 12:
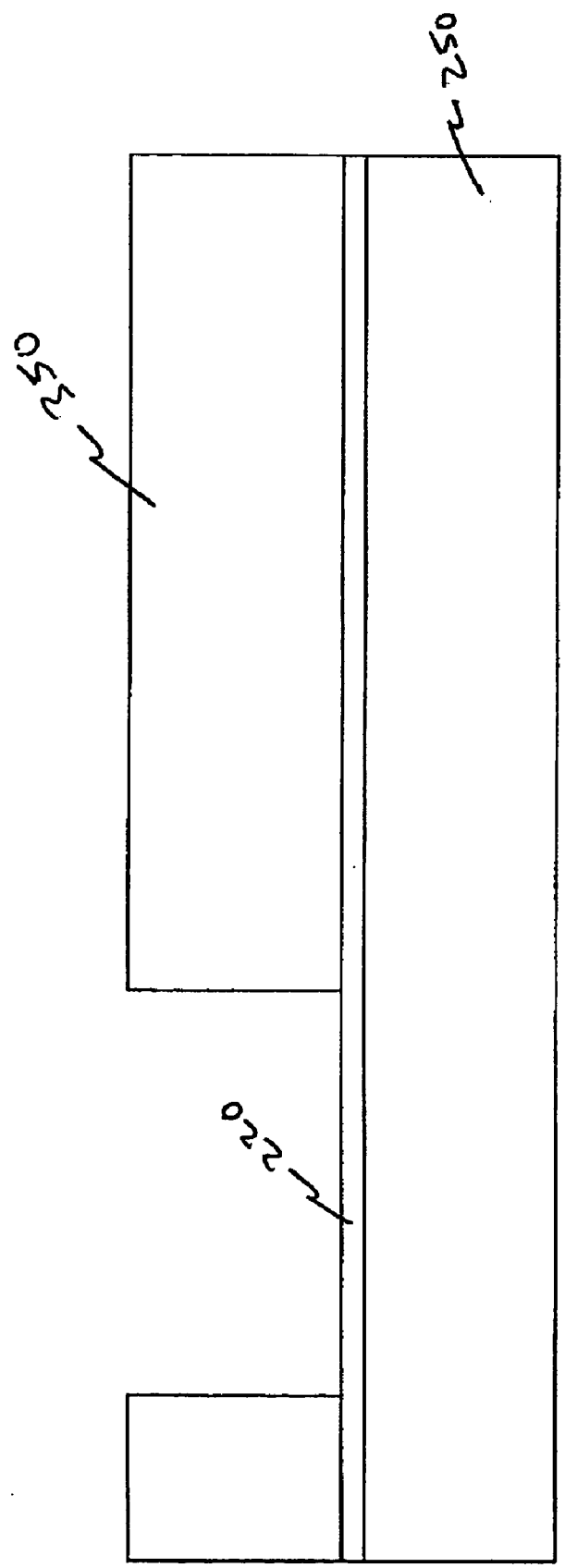
Figure 13:
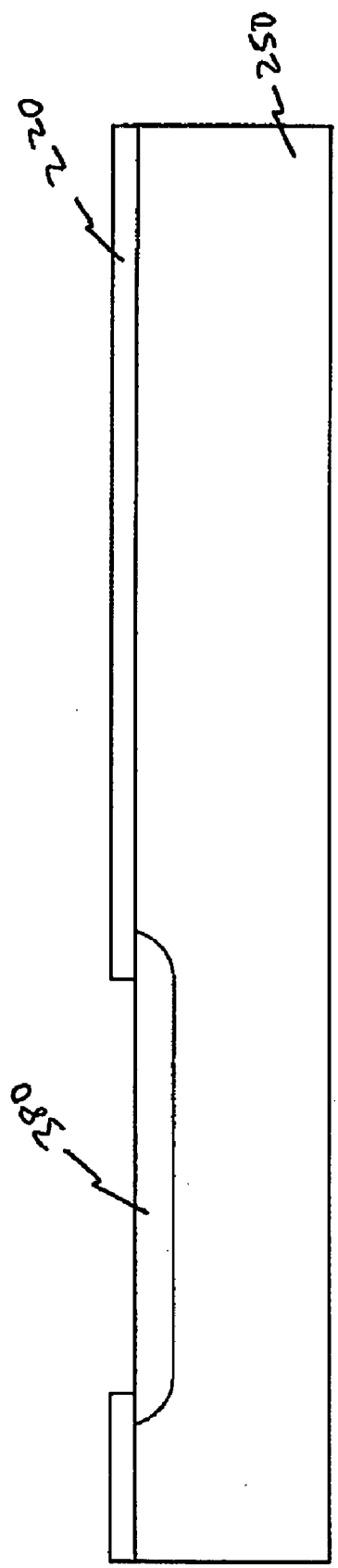
Figure 14:
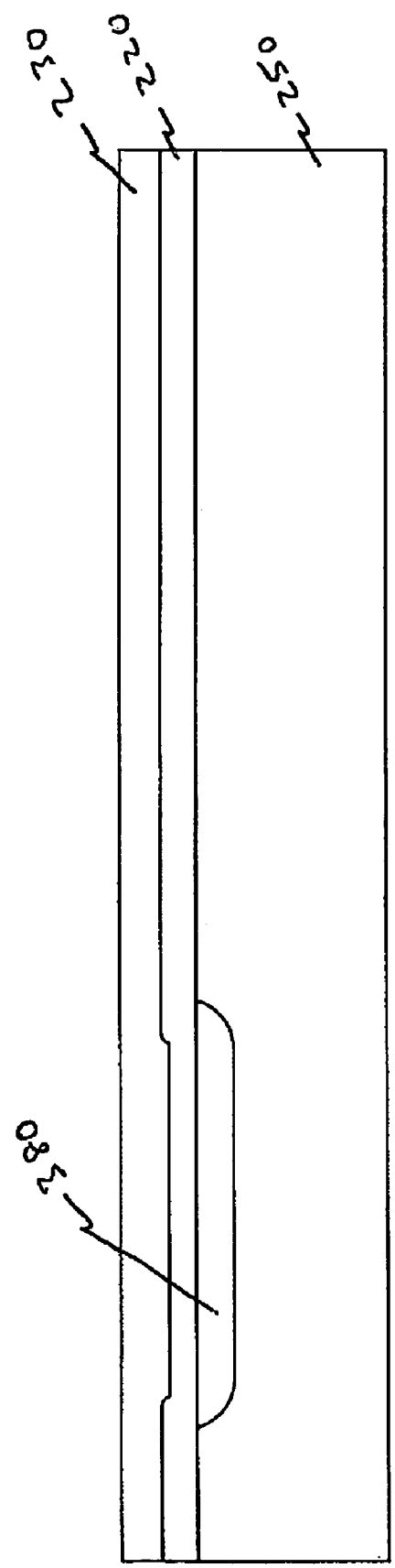
Figure 15:
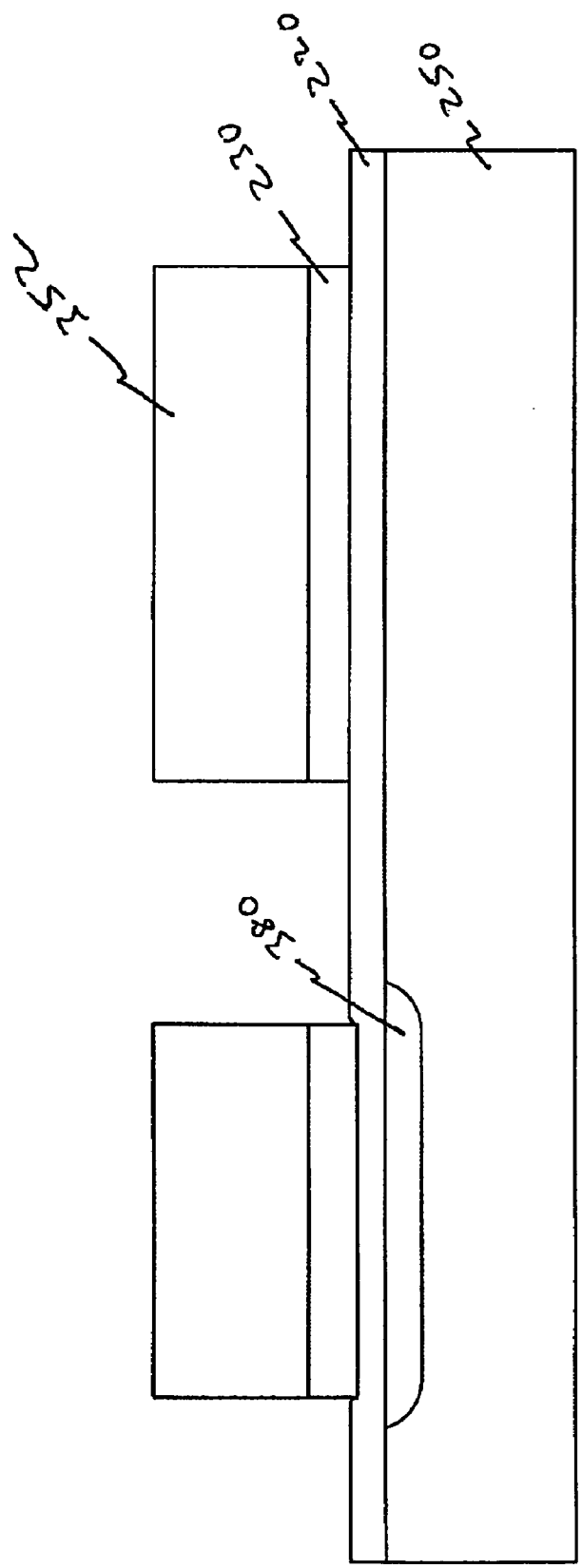
Figure 16:
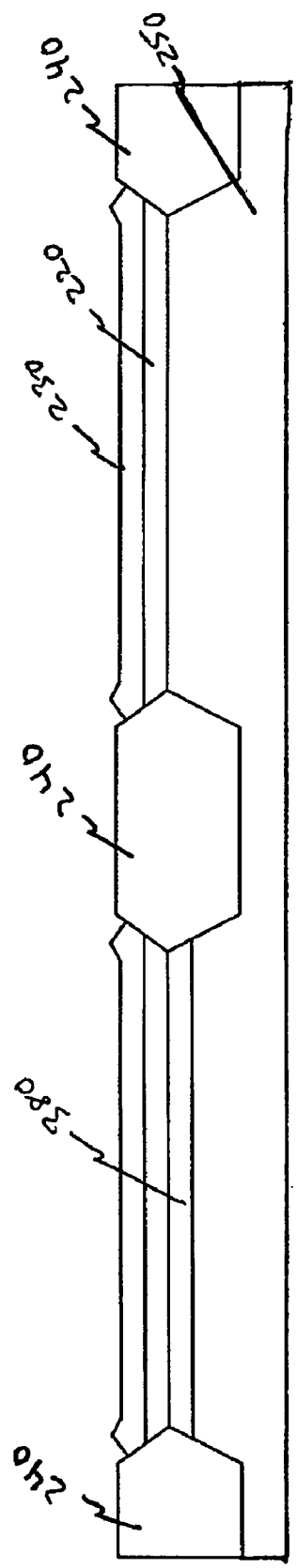
Figure 17:
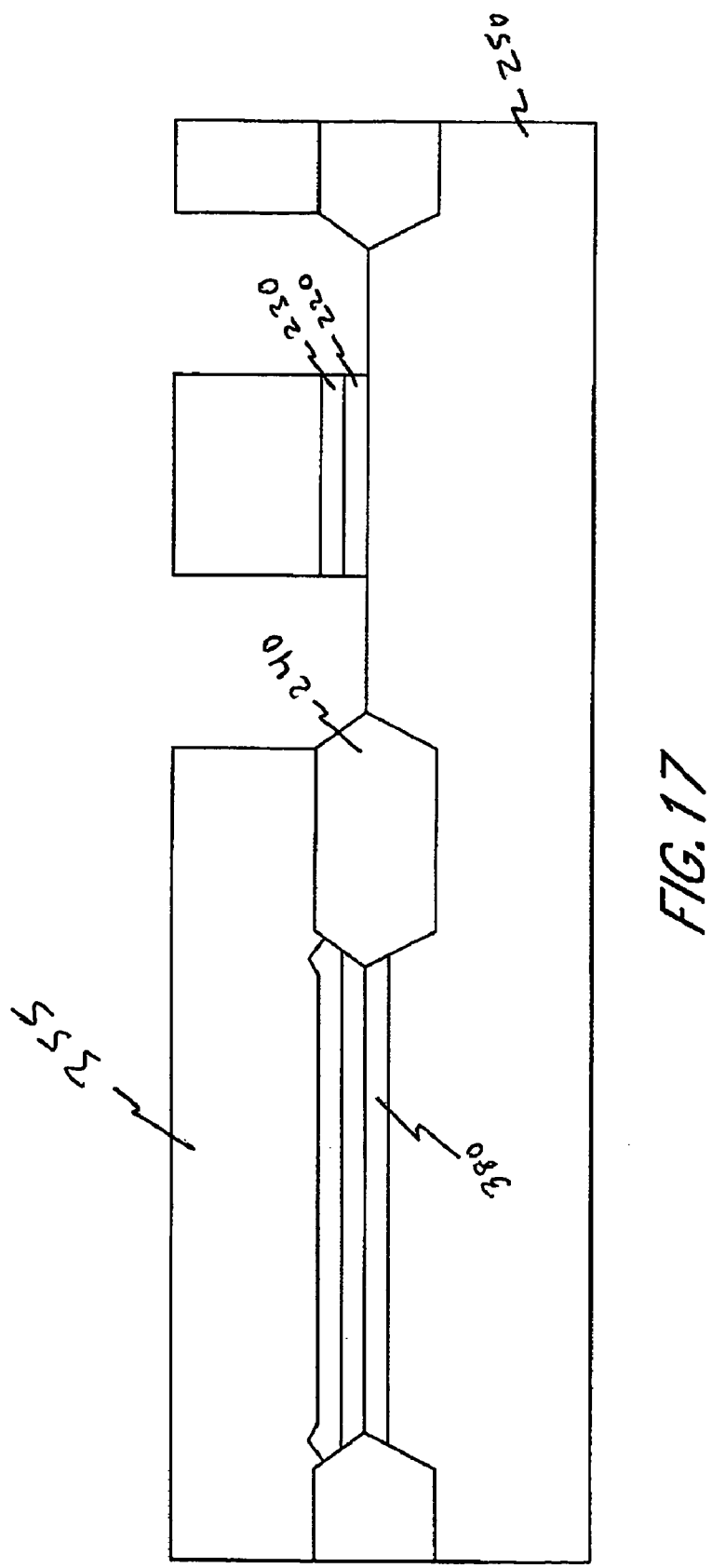
Figure 18:
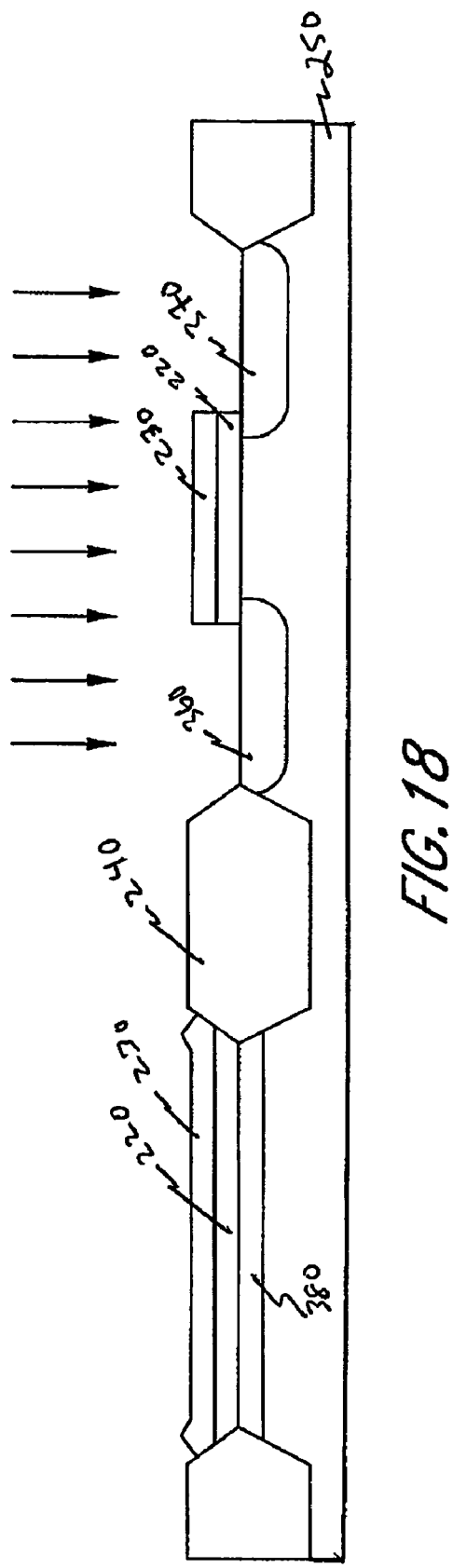
Figure 19:
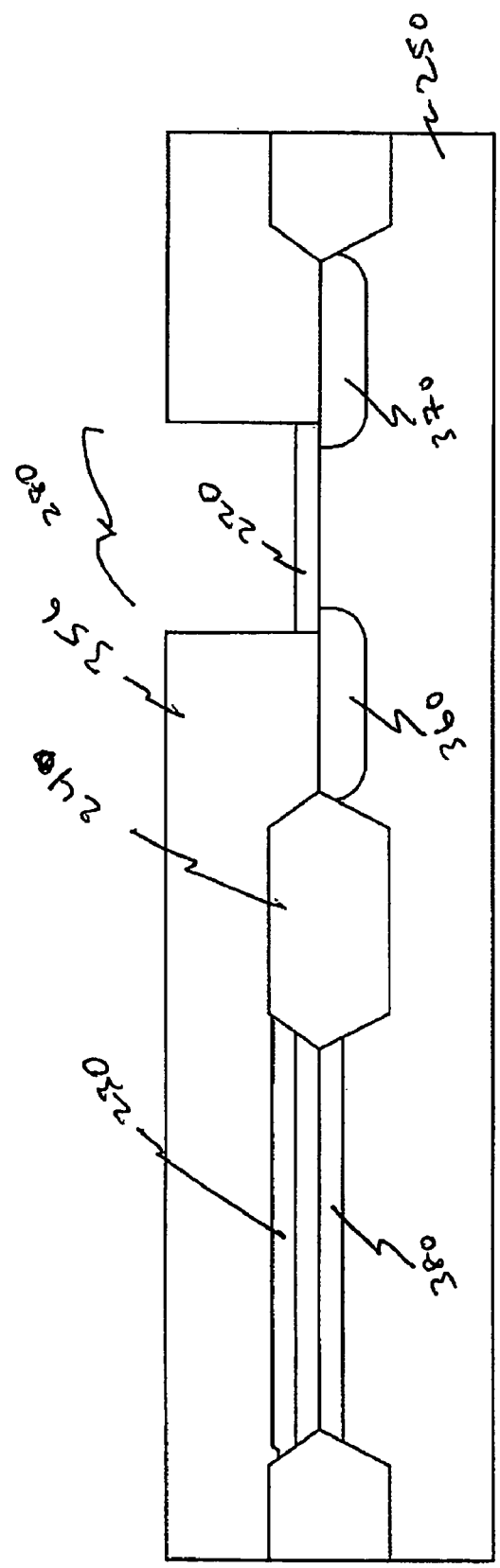
Figure 20:
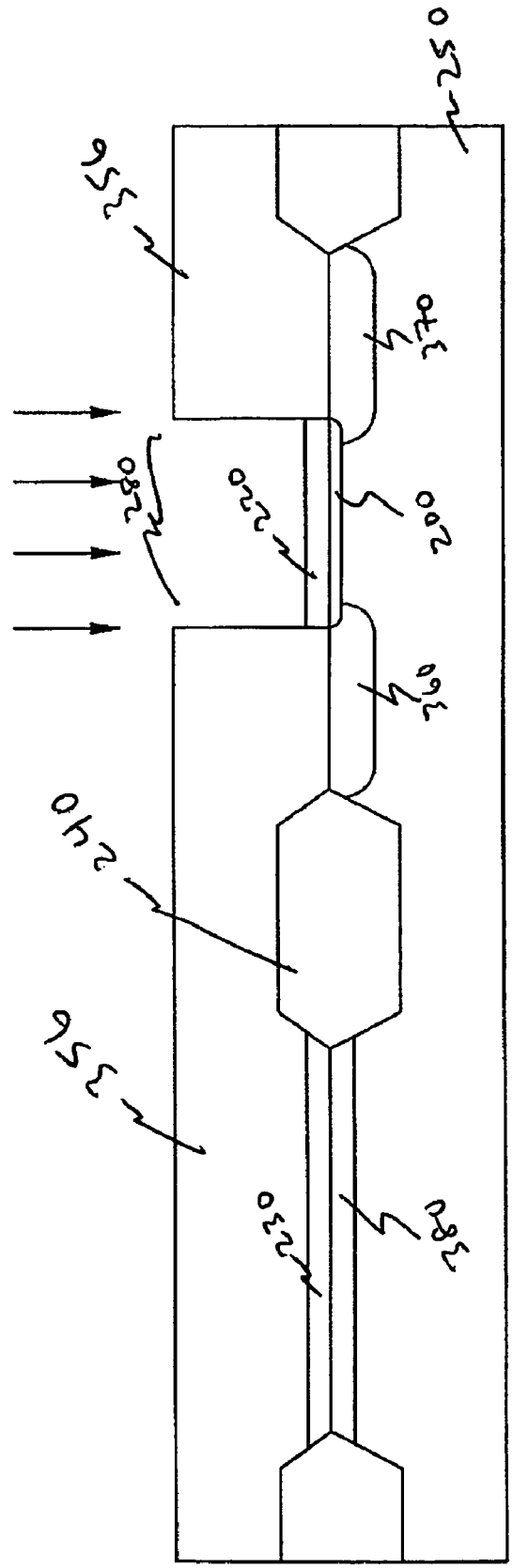
Figure 21:
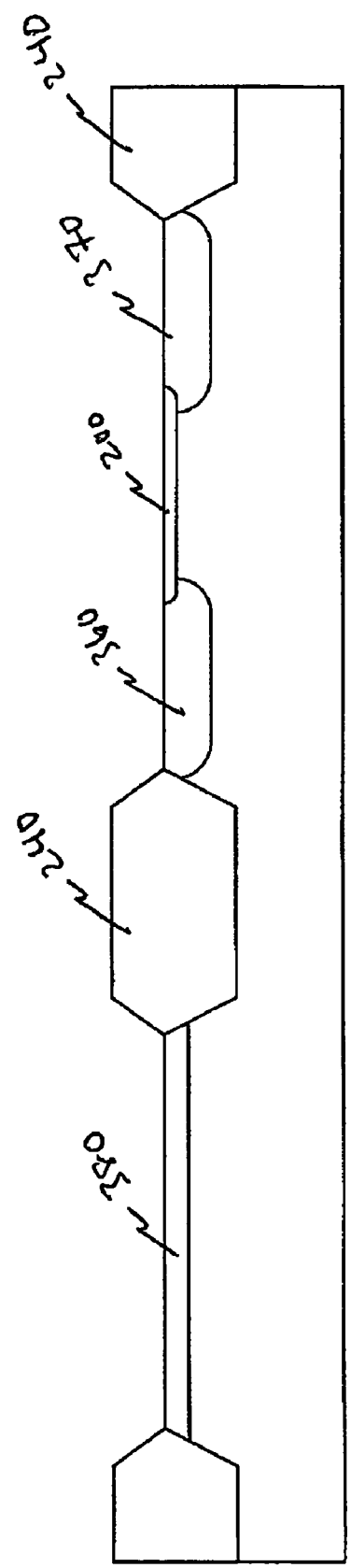
Figure 22:
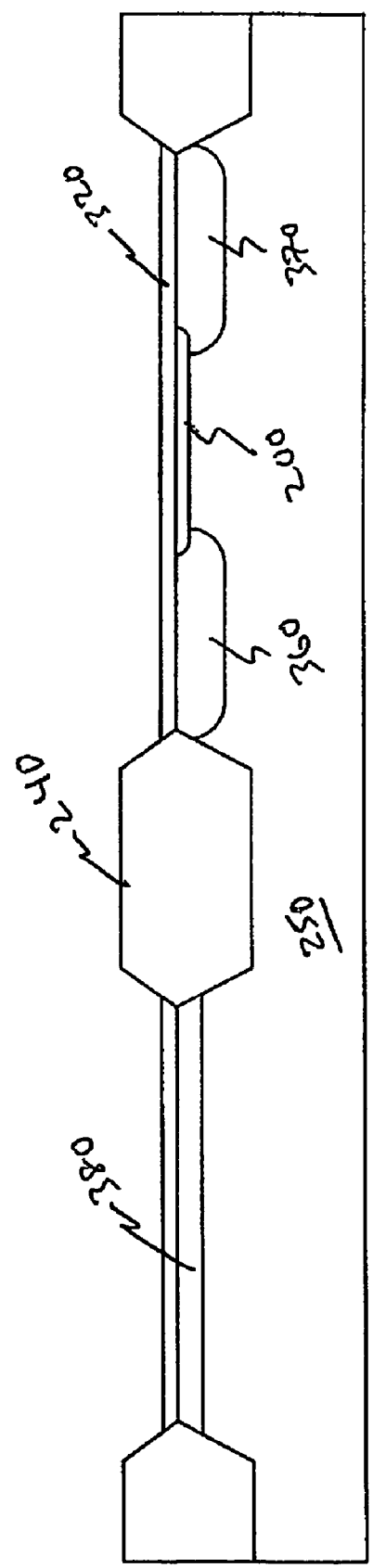
Figure 23:
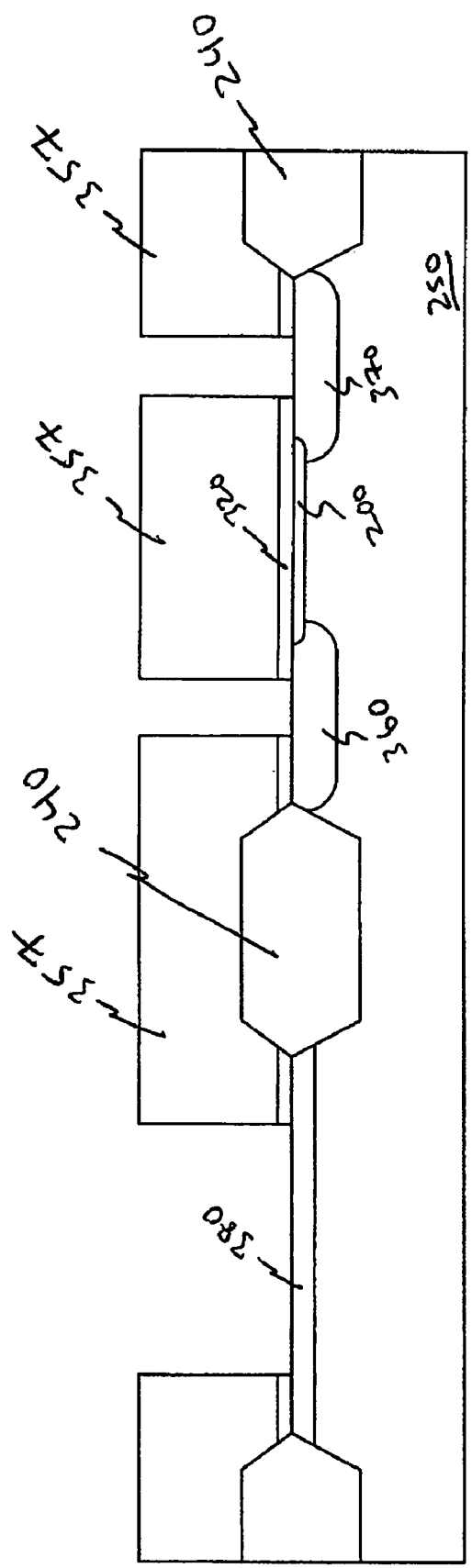
Figure 24:
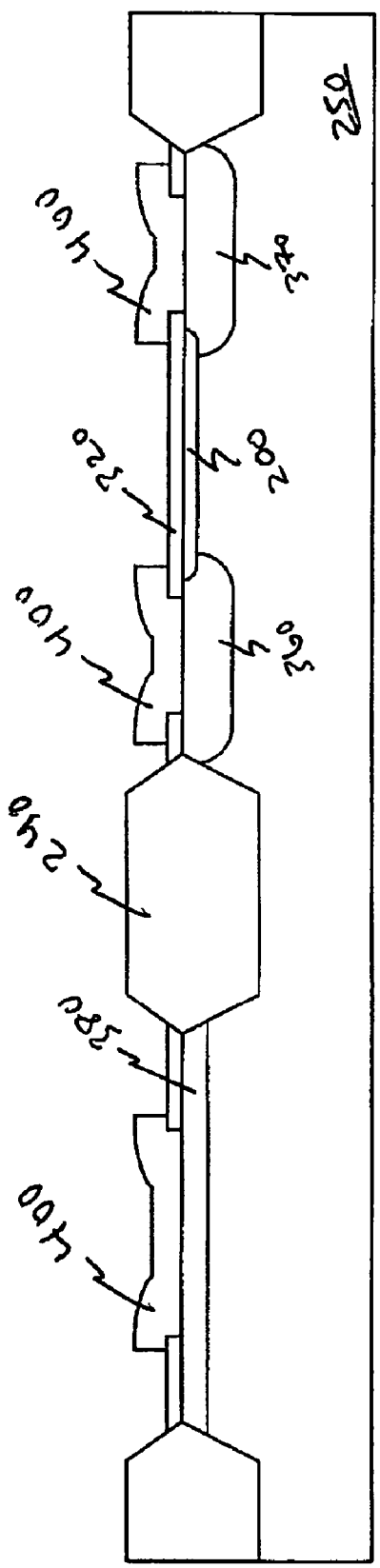
Figure 25:
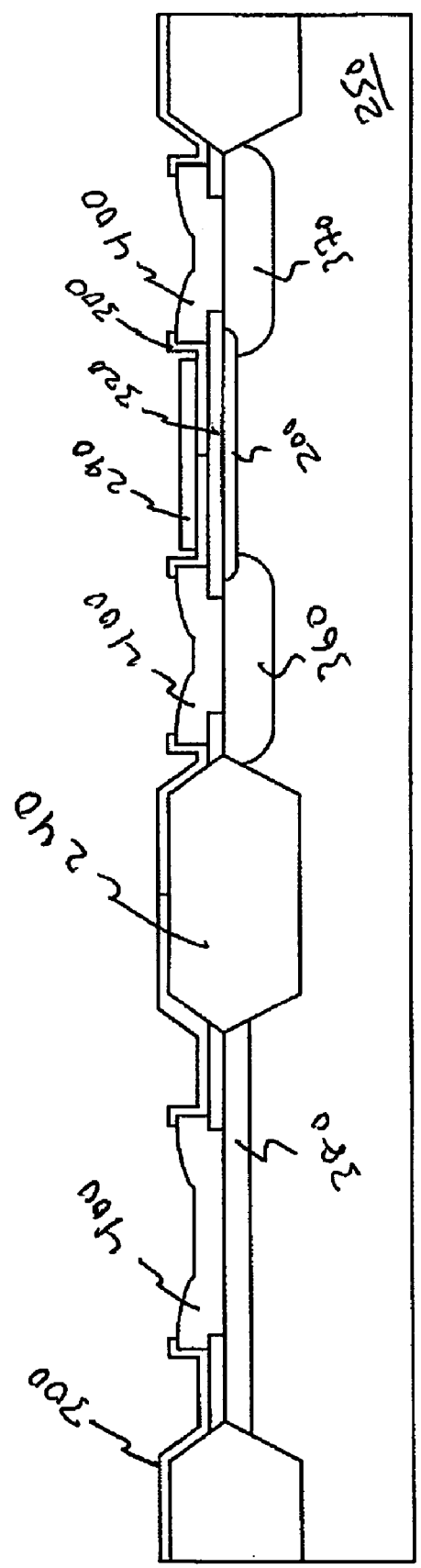

In FIG. 11, an oxide 220 is formed on a p-substrate 250. A photoresist 350 is deposited and patterned to create a substrate contact opening (FIG. 12). A p++ or N++ well 380 is formed in the substrate (FIG. 13) and the substrate is covered with a thin film of silicon oxide 220 and silicon nitride 230 (FIG. 14). A layer of photoresist 352 is deposited and patterned and the silicon nitride 230 is selectively removed (FIG. 15) over the areas in which the field oxide 240 is formed (FIG. 16). A second mask 355 is formed and the nitride 230 and oxide 220 are removed over the source and drain windows (FIG. 17) and the source 360 and drain 370 regions are doped appropriately (down arrows), as illustrated in FIG. 18. The source and drain region may be p or n doped depending on the particular device arrangement. The nitride layer 230 is removed over the active region 280 (FIG. 19), a third mask 356 is formed and a buried channel 200 is formed (down arrows; FIG. 20). The remaining oxide 220 is removed to produce the structure illustrated in FIG. 21. A gate oxide 320 is deposited (FIG. 22) and patterned through a fourth mask 357 (FIG. 23). Metal contacts 400 are formed as shown in FIG. 24. Next, sealing layer 300 is deposited and patterned with another mask (not shown) to expose the metal contacts 400 (FIG. 25). Finally, a polysilicon gate 290 is formed over the buried channel 200 as illustrated in FIG. 25. To form a sensor, recognition elements are subsequently attached to the gate 290 as described above.

It will be understood that other sequences, materials and processes can be employed to arrive at the desired structure.

As the majority of biological targets appear to be negatively charged at neutral pH, a conducting p-channel is utilized in the preferred embodiments. Here the attachment of negatively charged targets at the active region will add conduction to the p channel. However, one of skill in the art will recognize that other configurations of the transistor may be utilized depending on the particular circumstances. While a buried conducting p-channel as illustrated operates in enhancement mode for the detection of negatively charged targets, it would work in depletion mode for the binding of positively charged targets, as long as the device does not go into inversion. If desired, a particular sensor can be configured to signal the presence of a positively charged target (i.e., comprises recognition elements specific for a positively charged target). In these embodiments a conducting n-channel can be utilized such that the transistor operates in accumulation mode. Such channels can operate with a degree of surface depletion and provide a similar measure of attached targets.

In other embodiments the transistor operates in inversion mode via formation of a conducting inversion layer in a channel region upon target binding. In each of these embodiments, the transistor preferably operates in accumulation or depletion mode, but can operate in an enhancement mode given the correct doping of the source and drain contacts.

Manipulation of the bias on a back gate or side gate is preferably utilized to adjust the sensor sensitivity by adjusting the conductance and concentration of charge carriers in the channel as described below. For example, application of a back gate bias can reduce channel conductance, thereby providing a channel that is more sensitive to target attachment or chemical alteration of the gate material.

By measuring the reverse bias required to provide the same sensor parameter (e.g., current) as prior to target attachment, the back gate bias can also be used as the sensed parameter. Relative doping of the substrate and channel can be used to affect the sensitivity of this output parameter to channel conductance modulation by attached targets. For example, a lighter doped substrate requires a higher reverse bias change to achieve the same reset of the channel to the condition before target attachment. AC or DC voltages may be utilized. A sensor utilizing a reverse bias is illustrated in FIG. 29. In the illustrated sensor, recognition elements 10 are bound to an insulator 300 overlying a buried channel 200. The buried channel 200 overlies a depletion region 210, and is formed in an n substrate 250. A reverse bias (VR1) is applied from a power source 105.

The recognition elements may be bound directly to the active region over the channel of the transistor. Alternatively, linker molecules may be utilized to attach the recognition elements to the active region. In still other embodiments, the recognition elements are synthesized directly on the active region.

Recognition elements that are specific for the targets of interest are identified. Typically the recognition elements have been previously identified as capable of binding the target of interest, or, in some embodiments as capable of reacting with the target. However, in some embodiments new recognition elements capable of binding the target of interest are identified. For example, antibodies to a particular target may be produced by well-known methods. In another example, aptamers that are capable of binding the target of interest are identified by screening.

Once a recognition element has been identified, a sufficient amount of the recognition element is produced or obtained to form the sensors. The recognition elements are then applied to the active region of the sensor. Typically the active region of each sensor will comprise a single type of recognition element. However, in some embodiments, the active region of the sensor will comprise more than one type of recognition element. For example, in one embodiment, the active region of a sensor comprises two or more types of recognition element that are specific for the same target. In other embodiments the active region of a sensor comprises two or more recognition elements that are specific for different targets. One of skill in the art can readily determine the appropriate recognition element composition for each sensor based on the particular application.

The recognition elements are attached to the active region of the sensor by methods well-known in the art. For example, silanization of a surface may be utilized to attach recognition elements. In other embodiments, a streptavidin/biotin system is used. In yet other embodiments the recognition elements comprise a thin film that is deposited on the surface of the active region.

The active region preferably comprises a material to which the particular type of recognition element can be attached. The skilled artisan can choose this material. In one embodiment the recognition elements are attached to an active region comprising a polysilicon gate. The polysilicon gate may be n, n+, p or p+, where the doping is selected to affect the conduction of the underlying channel. For example, an inversion channel may be formed. In other embodiments accumulation may be affected, resulting in a more conducting channel and requiring a larger back gate bias to pinch off the conducting channel (with an attendant sensitivity increase).

In another embodiment the active region does not comprise a poly-Si gate and the recognition elements are attached to a gate dielectric layer, such as a silicon nitride layer. The surface to which the recognition elements are attached may be modified to facilitate attachment.

The recognition elements are preferably selectively attached to the active region, such that they are not present on other areas of the sensor. This may be done by masking the other areas (e.g., using conventional resist masks), attaching the recognition elements to the active area, and removing the mask. In another embodiment, recognition elements are selectively attached to the active area by controlling the application such that recognition elements are only provided to the active area. In the latter process, optical assists may be utilized, as known in the art. In still further embodiments, the recognition elements are selectively attached to the active area by selectively activating the active area for recognition element binding. An example of such selective activation is described below.

In one embodiment the recognition elements are selectively attached to the active region via linker molecules. Linker molecules are provided on the surface of the active region of the sensor. The linker molecules are then contacted with the recognition elements under conditions such that the recognition elements are bound to the substrate. In some embodiments the linker molecules comprise a protective group that must be removed prior to recognition element binding. The protective group may be removed, for example, by exposing the linker molecule to the proper activating conditions, such as light, radiation, electric fields, electric currents or other activators. By controlling the activating conditions, a defined region can be activated. For example, if the protective group is removable by light, a defined region of the substrate comprising the active area may be illuminated (e.g., through a lithography reticle or through a patterned mask on the substrate), thus activating the linker molecules in that area. A recognition element may then be contacted with the entire substrate, but will only bind to the activated linker molecules in the defined region. The defined region may be a particular region of the active region of a discrete sensor. In preferred embodiments, however, the defined region comprises the entire active region of one or more discrete sensors. In this way, a particular recognition element can be bound to one or more specific sensors in an array, without binding to the remaining sensors. A different discrete area of the substrate may then be activated, such as the active region of a second sensor. A second type of recognition element may then be bound to the activated region. The process may be repeated to form an array of sensors, each with a defined specificity, as discussed in more detail below.

In some embodiments, rather than attaching recognition elements that have been previously synthesized, recognition elements can be synthesized directly on the active regions of the sensors. For example, oligos can be synthesized directly on the sensor gates.

The sample to be analyzed is allowed to contact the active region of the sensor and the output signal is processed and interpreted. Thus, the active region is preferably accessible (e.g., by opening contact vias through an overlying insulating layer) after any higher level metallization.

The areas of the substrate and sensors outside of the active region 280 are preferably covered with a protective material 255, as illustrated in FIG. 31, to prevent undesirable interactions between the sample and the substrate. The protective layer may be, for example, the gate dielectric layer, an inert layer, a biochemical layer, a conducting layer, such as a metal layer or a conducting polymer layer, or a biochemical layer.

As discussed above, the gate dielectric may serve as a protective material 255. In other embodiments (not shown) the protective material 255 is an oxide that is deposited over the substrate and patterned to expose the active region 280 of the sensor. In still other embodiments the protective material 255 is an organic material that can be patterned to expose the active region 280. In some embodiment the protective material 255 is a polymer displaying an inert surface, such as parylene. In other embodiments the protective material 255 is a glass or epoxy material.

In preferred embodiments the protective layer shields the regions outside of the active region from the potentially adverse effects of charged compounds in the sample. This will prevent a semiconductor layer from being modified or affected electronically in a way which adversely affects a sensor or other device connected to the semiconductor layer. In some embodiments, the protective material 255 prevents binding of charged molecules from the sample to any region outside of the active gate region. In a particular embodiment the protective material 255 is a protein, such as an antibody, which does not bind with any compounds in the sample.

A conducting shield 257 or "electric filed blocking layer" may also be formed in the region surrounding the active region 280 of the sensor, as illustrated in FIG. 32. The conducting shield is arranged parallel to the substrate and extends in all directions away from the active region 280. In some embodiments the conducting shield covers the entire substrate surface except for any active regions. The conducting shield may be made of any conducting material, including metals and conducting polymers. The conducting shield 257 is preferably biased to prevent unwanted influence of attached molecules and materials in the region outside of the active sensor region 280. A voltage or ground may be supplied. In the illustrated embodiment a voltage is supplied by power source 105.

In addition to their application in conjunction with the sensor disclosed herein, the protective layer described above can be used in conjunction with any sensor where it is desirable to protect regions outside of the active sensor region from deleterious interactions with the sample.

In the preferred embodiments, the sensor output parameter is a voltage, current, transconductance or resistance change in response to binding of the target to one or more of the recognition elements. The sensor output results from the attached charge and/or a chemical potential change on the active region as a result of target binding.

For attached charge, the thickness of the region between the channel and the recognition elements is not important (especially if it is small compared to the active gate area dimensions). For chemical potential sensing, it is desirable to have the region between the recognition elements and the conducting channel as thin as possible. The thinner this region the larger the influence of the chemical potential (i.e., contact potential) on the channel conductance.

The sensitivity of the sensor can be tuned across a large dynamic range. The sensitivity may be modified, for example, by channel doping. In the preferred embodiments, the channel is doped with a dopant type to insure that a buried conducting channel is formed that operates in an accumulation or depletion mode. By operating in such modes, the device typically displays a linear resistance change in response to target binding when the FET channel is in the linear I-V region. Thus, the sensor is preferably operated without pinch off. However, in other embodiments target binding is determined based on a change in the saturation current. As used herein, "accumulation mode" indicates that binding of the target of interest enhances conduction in the buried channel between the source and the drain.

In embodiments in which the sensor comprises a conducting channel, the sensitivity is preferably enhanced by reverse bias of the channel/substrate PN junction. In these embodiments a back PN junction, or back gate, is used to reduce channel conductance, resulting in an increased proportionate signal upon substrate binding. Preferably, the initial conduction is kept low by manipulating the voltage on this back gate. For example, conductance through an implanted p conducting channel is reduced by applying a positive voltage to the back gate, which leads to increased partial depletion of the channel. In some embodiments, the bias or reverse bias is measured as a sensor parameter.

Preferably, the active region is made as small as possible to reduce costs, while remaining large enough to accommodate a sufficient number of recognition elements to produce a desired signal upon target binding. That is, by minimizing the active area, a high density of recognition elements can be obtained while minimizing the total number of recognition elements. Because some recognition elements, such as monoclonal antibodies, can be expensive, minimizing the total number required reduces the cost of each sensor.

In some embodiments, the sensor is configured to detect large targets, such as whole cells or bacteria. In these situations, the active region is made large enough to accommodate a sufficient number of targets to generate a detectable signal.

Gate shape may also be used to increase the output signal. For example, a large width/length (W/L) ratio provides increased output current and transconductance. Here, length refers to the distance between the source and the drain. Thus, in some embodiments the W/L ratio of the active region is increased to increase receptor sensitivity. In a particular embodiment the gate is shaped as a meander line to increase the width to length ratio. Further, such selection can be used to extend the linear region of the I-V characteristics. The latter provides ease of measurement through a simple ohmmeter. In general, the saturation region provides the highest measurement sensitivity. Preferably the W/L ratio is at least 2:1, more preferably at least 10:1, yet more preferably at least 50:1, even more preferably at least 100:1 and still more preferably 1000:1 or greater. In one embodiment the active region is 0.12 μM×0.12 μM. In another embodiment the active region is 0.12 μM×12 μM.

In FIG. 28, two active regions with the same width to length (W/L) ratio are illustrated. Because the W/L ratio is the same, the electrical properties of the two active regions will be the same assuming the same density of recognition elements. However, the smaller area requires fewer total recognition element molecules. Thus, a sensor utilizing the smaller active region area will have the same sensitivity but a reduced cost.

As discussed above, the sensitivity of the sensor may also be controlled by varying the surface density of recognition elements on the active region. The strength of the sensor output is directly related to the density of bound targets in the active region. Thus, by increasing the surface density of recognition elements 10 on the active region 50, as illustrated in FIG. 27, the sensitivity can be increased. In FIG. 27A, the active region 50 has a recognition element 10 surface density of N1 (recognition elements per square micron). In FIG. 27B, the active region 50 has a recognition element 10 surface density of N2. All possible binding sites for recognition elements on the top gate are filled (FIG. 27B). When the recognition elements 10 are fully occupied (saturated), the sensor in FIG. 27B has a signal N2/N1 time as great as the sensor in FIG. 27A. For example, if N1 is 12 and N2 is 10,080, the signal is increased by a factor of 840. Thus, by increasing the density on the same surface area, the sensitivity is increased by the ratio of the higher density to the lower density.

A high surface density of recognition elements 10 (FIG. 27B) can be utilized to make the sensor as sensitive as possible to the desired target. In preferred embodiments, recognition element density is as high as possible given the steric hindrance between recognition elements and limitations of the available methods of attachment. Preferably all binding sites for recognition elements are bound. In some embodiments the sensor is arranged to detect toxins at very low levels by utilizing a high density of recognition elements. For example, botulinum toxin can be toxic at a level of only 50 ng/L. In one embodiment a monoclonal antibody is used as the recognition element for detecting this low but toxic level of botulinum toxin. Antibodies are attached to the active region at a concentration of about 30,000 Abs per square micron. Assuming a dissociation constant of about 1 nM, a measurable 0.45% change in channel conductance would be observed upon contacting the sensor with a sample comprising 50 ng/L botulinum toxin. With an antibody with a better binding affinity, the change in channel conductance would be even greater. For example, at a KD of about 0.06 nM, this level of botulinum toxin would produce an approximately 2.5% change in channel resistance.

In other embodiments, sensitivity is increased after target binding by enhancing the charge of the bound target. This is referred to as "charge amplification" and is preferably used where the original target molecule is of low density, has low or no charge, or when the concentration of target is low. Charge amplification may be accomplished, for example, by contacting the bound target with a secondary charged molecule or complex that specifically binds to the target, which in turn is bound to the sensor. The secondary charged molecule may be, for example, a bead, a nanoparticle, a nanotube, a detergent, a protein, an aptamer, an oligonucleotide, a section of DNA or other nucleotide, or an antibody. In addition, the charge of the secondary molecule may be altered to further increase the signal. In a particular embodiment the secondary charged molecule is an antibody with modified charge. In some embodiments, the secondary charged molecule comprises a bead or other synthetic material that has been modified to have a desired charge. The bead is then derivatized with a molecule that allows the bead to specifically bind the target. In other embodiments the secondary charged molecule is a chemical which carries substantial charge, such as a nucleic acid. Upon binding to the target, which has bound to the recognition element, the secondary charged molecule increases the signal from the sensor proportionate to the charge that it carries. In other embodiments, the secondary charged molecule is introduced to the sample and allowed to bind the target, if present, prior to contacting the sensor with the sample. Coatings, such as detergent or lipids, may also be used to increase particle carrying charge.

The ability to enhance the sensitivity of the sensor allows for the identification of small amounts of a target of interest in a sample. The sensor can theoretically be tuned to detect at least as few as 100 electronic charges. Detection down to 1-10 pM of target is achievable.

The percentage of recognition elements that are bound by target depends on the concentration and the strength of the interaction between the recognition element and the target. By increasing the target concentration, the bound target density is increased, leading to a stronger signal.

It is possible to increase the ability of the sensor to detect low concentrations of a target in a sample by concentrating the target molecules in the vicinity of the active region. This may be useful, for example, in detecting very low lethal concentrations of a toxin such as botulinum toxin. In addition to increasing the signal strength, concentrating target molecules in the vicinity of the active area increases the speed of the sensor.

Because most target molecules are charged or can be made to carry a charge, such as by contacting them with a charged binding agent or by adjusting the pH of the sample, an electric field can be utilized to move the charged target toward the active region of the sensor. An electric field can be generated using a battery or a power supply. The electric field can be DC or AC, including sinusoidal and pulsed fields. The voltages creating the electric field can be of either polarity and may have a time dependent character. By selecting the appropriate polarity, the concentration of selected species can be controlled, as positive and negatively charged molecules will drift in different directions. Preferably, the electric field does not adversely affect the specificity of the recognition elements for the target.

AC and pulsed voltages will have different effects on different species with different charges and mobilities and thus may be utilized to separate chemical species, for example by attracting the target while repelling other species.

In one embodiment an electrode is associated with the active region of a sensor. As illustrated in FIG. 33, a target species S1 can be caused to move toward the active region by applying an electric field E. The concentration C1 of species S1 at the sensor surface (X=0) is directly related to and dependent upon the strength of the electric field E and the diffusion coefficient of the target in the sample. The greater the electric field, the larger the concentration of the target at the active region. Thus, in one embodiment an electric field is generated in the immediate vicinity of the active area.

However, in some cases electric fields can interfere with target binding to recognition elements. For example an electric field can change the structure of a charged protein such as an antibody or nucleic acid. As a result, in other embodiments the electric field in the vicinity of the active region is reduced or is zero. Another way to deal with this problem is to utilize a grid electrode structure to keep the active region at a constant voltage and without the applied electric filed terminating on the sensor surface, as illustrated schematically in FIG. 34A. The electrode is not functionally tied to the sensor itself.

In the voltage biasing arrangement illustrated in FIG. 34A, the sensor and grid G1 are at ground and the solution is biased at a net applied voltage V. The grid structure G1 acts as a voltage terminal and is connected to the sensor to provide a zero electric field between the active region of the sensor and the grid structure G1. The target species concentration builds up at the grid electrode G1 as shown in FIG. 34B. Actual delivery of the target species S1 to the receptors occurs by diffusion. However, since the target species at the grid G1 can be made high and the grid can be placed in close proximity to the active region, the result is an increased binding rate, higher concentration of bound target, and a resulting stronger and faster sensor output signal. The distance between the electrode G1 and the active region is preferably small to increase diffusion of target to the recognition elements on the surface.

In another embodiment, the grid is replaced by a cage as schematically illustrated in FIG. 35A. The cage configuration preferably results in concentration of target molecules as illustrated in FIG. 35B. In particular the concentration of target species is increased dramatically in the vicinity of the sensor and the target is unable to leave the cage once it is drawn in. Again, the distance between the cage and the active region is preferably small.

In another embodiment, the first electrode grid or cage is utilized in conjunction with a second electrode at location L in the sensor environment, as illustrated in FIG. 36A. In some embodiments the additional electrode is a grid (G1), while in other embodiments it is a cage (CG1) or wire. Additional electrodes at additional locations can also be used (G3, CG3 etc. . . . ). FIG. 36B illustrates the concentration profile resulting from the use of additional electrodes.

In these embodiments, a first voltage is applied between the first and second electrodes to cause charged molecules, typically the target molecules, to drift to the location of the first electrode, a distance 6 from the active region. If a second cage is used (FIG. 36B), target transport occurs in three dimensions. The location of the second electrode and the applied voltage between the first and second electrodes determines the electric filed and the rate of drift of the charged species to the active region. If desired, a second voltage can be applied between the sensor itself and the first electrode if desired.

Figure 37A:
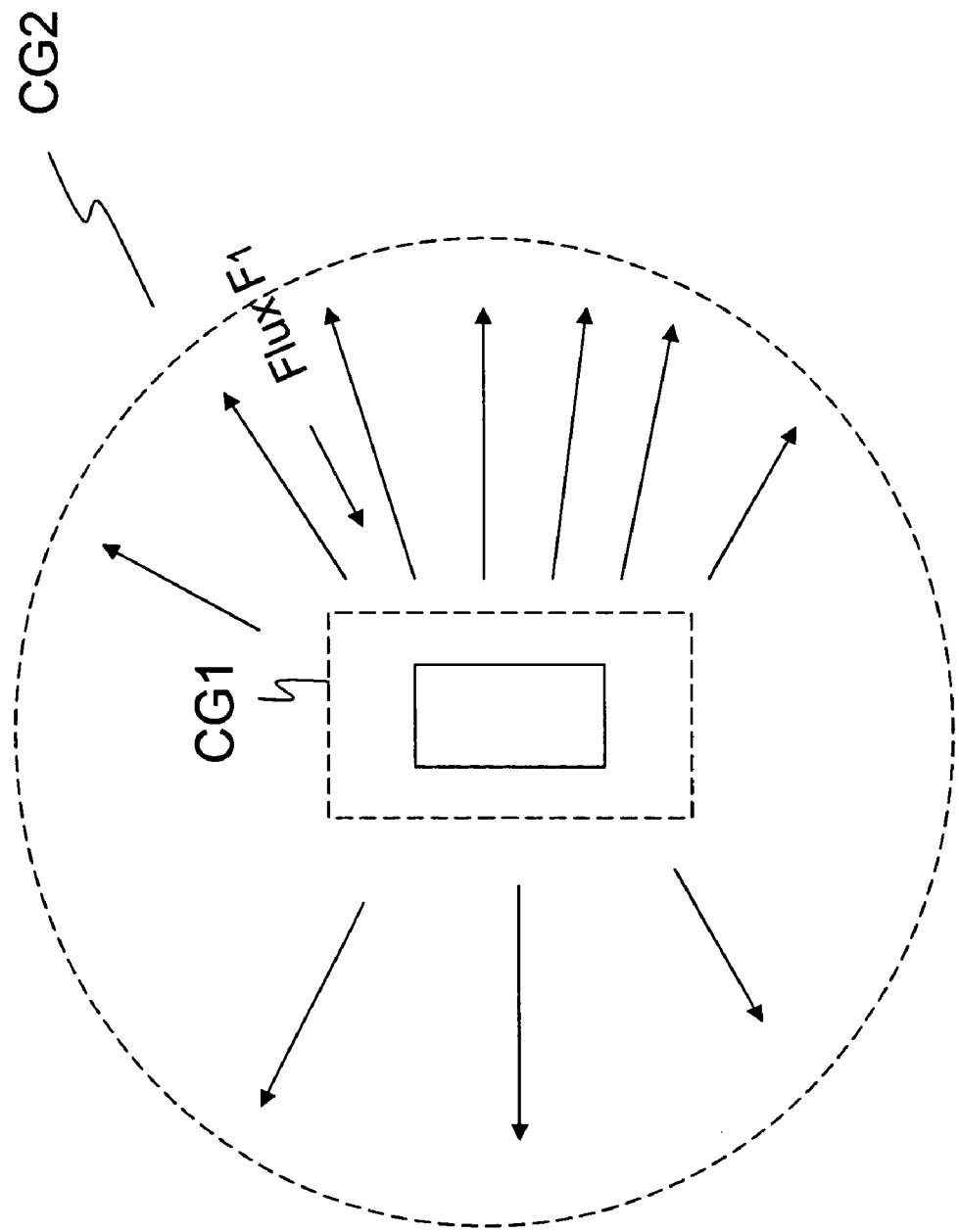
Figure 37B:
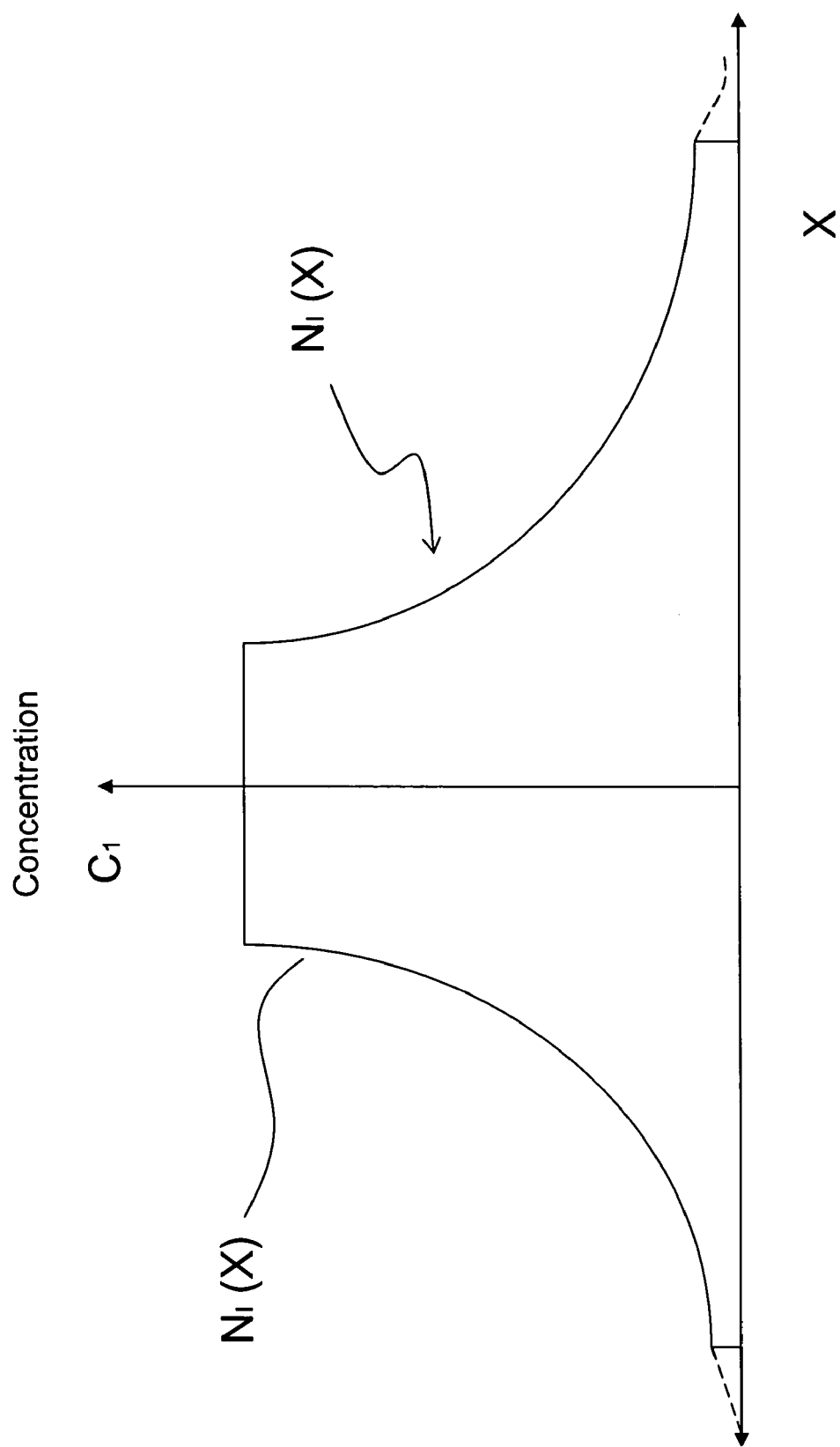

FIG. 37A illustrates an embodiment in which the active region and a first cage (CG1) are in close proximity. A second cage (CG2) is located at a distance L (CG2 is spherical in the illustrated embodiment, although other geometries could be used). The electric field (E) profile as a function of radius (R) is illustrated in FIG. 37B. This arrangement allows for the analysis of a very large volume sample at a modest applied voltage value while providing the electric field necessary to collect target molecules from a three dimensional volume and concentrate them in the first cage location close to the active region of the sensor. Target accumulation speed is influenced by the applied voltage values. Thus, by increasing voltage target accumulation can be increased.

In other embodiments a third electrode, preferably a grid or cage, is added outside of the second, as schematically illustrated in FIG. 36A. A first voltage is applied between the first electrode and the second, and a second voltage is applied between the second and third electrodes. Additional electrodes can also be employed.

In other embodiments, an inhomogeneous electric field is created to drive target molecules to the desired area close to the active region of the sensor. This allows for a large accumulation of target molecules at a relatively low voltage. In a preferred embodiment a pointed electrode is utilized. However, it will be apparent to the skilled artisan that other electrode geometries can be employed.

In each of the embodiments utilizing additional electrodes, the electrode can be fabricated according to standard techniques using any material that can be biased. Typically the material utilized will be non-corroding. For example, and without limitation, a wire grid constructed of steel mesh or metal plated polymer mesh may be used. In other embodiments a MEMs grid can be fabricated in close proximity to the active region of the sensor.

In other embodiments a mechanical mixer is utilized to ensure that the entire sample is allowed to contact the active region of the sensor. This is especially preferred when non-homogeneous samples are to be analyzed.

Arrays

In preferred embodiments, an array of sensors is formed on a single semiconductor substrate and fully integrated with the appropriate addressing and information output circuitry. Memory devices, logic circuitry, readout circuitry, and other appropriate circuitry can be integrated as well, or connected through hybrid means. It is within the skill of one in the art to prepare the circuitry to suit their particular circumstances.

In one aspect, "array" means a predetermined spatial arrangement of sensors present on a substrate. In the preferred embodiment the sensors are formed in a silicon substrate. However, in other embodiments the sensors are formed separately and attached to a solid support in a hybrid architecture. Preferably, the array is addressable. That is, the location and specificity of each sensor is known. However, the specificity of the sensors present at each location is known or may be determined. In one embodiment an addressable location comprises more than one type of sensor. In another aspect, "array" can refer to the spatial arrangement of recognition elements on the active region of a particular sensor.

The sensors in the array may all be specific for the same target. That is, each of the recognition elements in the array may comprise recognition elements that are specific for the same target. This arrangement may be used, for example, in the case of an array that is designed to detect a single target. The presence of multiple recognition elements with the same specificity provides redundancy and confirmation of the presence of the target.

In other embodiments, the array comprises sensors that are specific for different targets. Such an array could be used to detect and/or identify more than one target in a sample. An exemplary array is illustrated in FIG. 9. This array comprises multiple rows and columns of sensors, each of which comprises recognition elements that are specific for a particular target. Addressing enables the identification of which transistor is affected, and how, by exposure to the sample.

The array may comprise multiple sensors that are specific for the same target. For example, in the array illustrated in FIG. 9 each of the sensors in a particular row comprises the same recognition element. This redundancy provides confirmation of the presence of a particular target.

In addition, the array may comprise sensors with orthogonal recognition elements. This is illustrated in FIG. 9, where the sensors in the first row 400 each comprise the same type of recognition element, while the sensors in the second row 500 each comprise an orthogonal recognition element. Thus, each of the sensors in the first and second row will signal the presence of the same antigen. However, each of the sensors in the second row comprises a recognition element that recognizes a different portion of the target recognized by the recognition elements on the sensors in the first row 400. For example, each of the sensors in the first row 400 may comprise a first antibody to a target of interest while each of the sensors in the second row 500 comprises a second antibody that differs from the first but that is specific for the same target of interest. The presence of orthogonal recognition elements provides for additional redundancy and avoids false positives or negatives that may be associated with a single recognition element type.

In other embodiments the array comprises sensors with recognition elements that allow for the confirmation of the detection of a particular target based on the presence of a second target. In these embodiments one or more sensors or groups of sensors in the array are specific for a first target, while one or more different sensors or groups of sensors are specific for a second target. Here, the second target is one that would not be present in the sample unless the first target is present. This enhances the redundancy of the test and avoids false positives. For example, if a recognition element for a particular infectious agent, such as a virus, is present on one sensor or group of sensors in an array, sensors with recognition elements to a protein that is produced by a patient in response to infection may also be included as another and related target. Thus, a sample from a patient could be screened for the presence of the infectious agent and a positive signal could be confirmed by the presence of the associated protein.

An array can comprise a low-density number of addressable locations, e.g. 1 to about 100, medium-density, e.g. about a hundred or more locations, or a high-density number, e.g. a thousand or more. Typically, the array format is a geometrically regular shape, which may facilitate, for example, fabrication, handling, stacking, reagent and sample introduction, detection, sensor addressing architecture and storage. The array may be configured in a row and column format, with regular spacing between each location. Alternatively, the locations may be arranged in groups, randomly, or in any other pattern. In one embodiment an array comprises a plurality of addressable locations configured so that each location is spatially addressable for high-throughput handling. Sensors may be identical in electronic architecture or vary according to their desired function.

FIG. 10 illustrates a group of four sensors with different geometric features on a single silicon chip. In particular, the size and shape of the active area 600 varies among the illustrated sensors. An array may constitute an array of either component members of the chip shown, or an array of the group, thereby forming an array of groups of sensors rather than an array of individual sensors. Such sensor group array components may comprise sensor configurations that vary according to the sensor objectives, sensitivity issues, and recognition element binding issues or other desirable features. While the sensors of FIG. 10 are of particular geometries, the geometries are not limited. Various active gate geometries and electrical contact pad geometries may be used. By way of example, active areas with a large W/L ratio increase the length of the linear I-V region and allow for commercial ohmmeters to be used for measurement instrumentation.

In a preferred embodiment, sensors that are specific for a particular target are grouped together on the substrate. The substrate may be a chip or a hybrid system. For example, all of the sensors that are specific for a particular target may be located in a single row on the substrate. Sensors are specific for a particular target if each of the sensors comprises recognition elements that are specific for one particular target. The signals from all of the sensors that are specific for a particular target may be combined to provide an enhanced signal indicative of the presence of a specific target. In other embodiments, the signals are maintained separately.

In other embodiments, the sensors that are specific for a particular target are not grouped together.

In a preferred embodiment each of the sensors in the array are connected to addressing circuitry that allows for the collection and analysis of a signal from each sensor. Based on the signal, the presence of one or more targets of interest is determined. Depending on the arrangement of the array and the design of the sensors, the nature of the target and the amount of the target may be identified as well. For example, sensors may be included that generate a signal only in the presence of a specific minimum concentration of target, as discussed above. The activities of sensors that are tuned to a particular concentration of target provide an indication of the minimum concentration of target in the sample. If a sensor tuned to a higher minimum concentration is not activated, a maximum target concentration can also be determined. By way of example, the presence of a toxin in a potable water supply may be hazardous if the toxin exceeds some critical concentration, but not hazardous in lower concentrations.

Configurations with multiple recognition elements on a single sensor may be useful, such as when identifying tainted blood in blood donors or samples. Any signal indicates the presence of one disease, and a blood donation is not taken or is discarded.

Typically, each sensor in an array comprises one type of recognition element. In this case, the number of sensors is at least as great as the number of different types of recognition elements to be used to identify the targets of interest, and thus at least as great as the number of targets to be detected. For example, if the presence of ten targets is to be detected in a sample, at least ten sensors with recognition elements specific for those targets will be present on the substrate. However, if orthogonal recognition elements are utilized to provide confirmation of binding of a particular target, the number of sensors will be higher. The number of sensors will be determined, for example, by the number of targets to be detected and the physical size of the substrate on which the array is formed.

Particular array spacing may be selected for either chip integrated sensor arrays or hybrid arrays. Such spacing may be selected to register with chemical delivery systems or "spotters." For example, a hybrid sensor array may have sensors distributed with the same architecture as a particular microtiter plate.

In one embodiment, at least one sensor comprises more than one type of recognition element. Here, the sensor may comprise two or more types of recognition element that are specific for the same target. Alternatively, the sensor may comprise recognition elements that are specific for two or more targets.

Each sensor in the array may be designed to provide the same signal upon binding of a target of interest. In another embodiment, the signal provided by each sensor or each type of sensor is variable and may be of a preselected magnitude.

Addressing circuitry enables large numbers of sensors to be included in an array on a single substrate (integrated chip or hybrid). Thus, the overall size of the array is not limited and will be determined based on a variety of factors, including the number of sensors, the physical size of the sensors, and physical constraints on the size of the substrate and the chemical preparation methods and equipment used. For example, the total size of the substrate and number of sensors may be limited by the available sample size. The total size may also be limited by the circuitry required to link the individual sensors. The total size may be limited by some minimum spacing between sensors as required by the methods for attaching recognition elements. In one embodiment, the sensors are present on a substrate with an area of about 100 cm$^2$ or less. In another embodiment the sensors are all present on a substrate with an area of about 10 cm or less. In a further embodiment the sensors are all present on a single chip of a few millimeters square. Other hybrid and integrated chip sizes addressing particular testing or manufacturing environments will be apparent to the skilled artisan.

For detecting the presence of one or more target s in a sample, the sample is contacted with the array of sensors and the electrical properties are measured at each sensor. If a change in the electrical properties is identified at any sensor, the target that interacts with the recognition elements on that sensor is identified as being present in the sample. Processes may be developed which avoid false signals arising from extraneous influences such as pH change, buffer used and sample stoichiometry and materials.

In another embodiment, the measured signal is a summation of the signal from all of the sensors. In this case, a signal indicates that at least one of the targets of interest is present in the sample. The type or magnitude of the signal may also be interpreted to determine which targets are present in the sample.

In one embodiment, the instrumentation is configured to selectively sample for particular sensors or groups of sensors within the array, and thus for particular targets. The configuration may be the result of the physical architecture or may be the result of electronic sensor measurement with subsequent logic determining which of selected sensors are being addressed. A particular set of sensors specific to a particular target and its cofactors or associated targets may be selected. Subsequent chemical processing may be used to provide confirmatory information. For example, pH change may be used to change target charge sign or magnitude or to determine the isoelectric point of the target. An expected change in charge or the identification of an expected isoelectric point can confirm the presence of a particular target and help avoid false positives. An example of the change of the charge associated with a target, here streptavidin, as a function of pH is shown in FIG. 30. In the illustrated example, as the pH changes from 1 to 14, the charge on the streptavidin molecule goes from highly positive to highly negative.

Applications

The analysis of samples for the presence of one or more particular targets finds uses in a wide range of fields, from medical, basic biological research, pharmaceutical, agricultural, environmental, homeland defense and industrial diagnostics to genomics and proteomics.

The arrays of the invention are useful for diagnostic applications and for use in diagnostic devices. In one embodiment the arrays are used to establish a correlation between the presence of a particular target, such as a pathogen or a particular protein, and a disease or a particular stage of a disease. In a further embodiment, once a correlation between the presence and/or amount or density of a target and a particular disease or a particular stage of a disease has been made, or is known, the arrays of the invention may be used to diagnose a particular disease or a stage of a disease in a tissue of an organism. In addition to diagnosing disease in humans and other animals, the arrays can be used in agriculture to diagnose disease in plants. For example, a crop seed sample can be tested for the presence of crop disease.

Accordingly, in one embodiment, the invention provides a method of diagnosing a disease or disorder in a patient. Multiple diseases can be screened for at the point of care and results provided immediately, allowing medical personnel to quickly select the most appropriate treatment options. One or more targets that are known to be associated with the disease or disorder from which a patient is believed to be suffering are selected. For example, if a patient is suspected of suffering from a viral infection, the methods of the present invention may be used to identify the presence of one or more proteins that are known to be associated with the infectious agent are selected for identification. For example, a sample from a patient suspected of being infected with HIV may be analyzed for the presence of one or more proteins known to be associated with HIV.

Similarly, the sensors and arrays may be used to evaluate the efficacy of treatment. For example, the presence of one or more targets known to be associated with a disease or disorder determined in a biological sample from a patient prior to and after treatment. This may help determine the efficacy of particular treatment options.

In other embodiments the sensors and arrays are used to identify particular targets the presence of which serves as the signature characteristic of a bodily state. For example, certain target proteins can be identified that are indicative of impending heart attack or stroke or that provide confirmation that a stroke or heart attack has already occurred.

The sensors may also be used to compare the expression patterns of proteins in different populations of cells or tissues. For example, cells may be subject to different conditions and the expression pattern of particular proteins compared to the protein expression pattern of a control cell or population. For example, the protein expression pattern of a cancer cell may be compared to the protein expression pattern of a control cell or population.

The ability to compare the expression of particular proteins between two cells or two population of cells may be useful in the identification and validation of new potential drug targets, as well as for drug screening. In particular, a protein may be identified which is expressed in diseased cells but not in normal cells. Such a protein may be a target for drug intervention; such as with inhibitors targeted to such a differentially expressed protein and the effect of different drug candidates on protein expression may be observed.

In some embodiments the arrays are used to screen human samples, such as blood, plasma or even breath, to identify a virus responsible for infection. For example, and without limitation, the arrays may be used to determine if an illness is the result of infection with SARS, influenza, NORWALK virus, Dengue virus or West Nile virus. Other infectious agents that can be identified by the sensors and arrays will be apparent to the skilled artisan.

In a particular embodiment, the arrays may be used to screen environmental samples for the presence of one or more toxic agents or pathogens, such as botulinum toxin, ricin and anthrax, for example in bioterrorism defense or environmental remediation. The arrays allow for the simultaneous detection, identification and quantification of the potential agents in the sample. In addition, the ability to build in redundancy decreases the risk of false reporting, including both false positives and false negatives.

In another particular application, the arrays are used for blood bank screening. If a potential donor has recently contracted a disease or disorder, such as HIV or hepatitis infection, traditional assays may not be able to detect the infection. An array comprising one or more sensors that are specific to a multitude of blood born diseases is prepared. Thus, a single array can be used to screen for multiple diseases. A blood sample is obtained from the potential donor, such as by finger prick, and contacted with the array. A positive signal from the array would indicate the presence of a disease and the donation would be rejected. As the presence of any one of the diseases that are screened would be sufficient to reject the donation, it is not necessary to have an addressable array and costs can be reduced. However, if an addressable array is used, the identity of the disease or disorder can be readily determined and the potential donor can be counseled accordingly.

Similarly, animals including both pets and food animals can be screened for the presence of disease. For example, routine screening of cattle and other food animals for diseases such as mad cow disease (by identification of the presence of prions) can be affected. In some embodiments, samples of effluents from a group of animals, such as those from feedlots, may be tested for tainted animals prior to the screening of individual animals. In this way, individual screening is only carried out if it is determined to be necessary, thereby saving time and money.

In an industrial setting a product or intermediate may be analyzed for the presence of a particular compound.

The sensors and arrays will find use in many public health applications. For example, foodstuffs may be sampled for contamination and effluent water that is used to wash imported vegetables may be sampled for the presence of human pathogens. Similarly, drinking water or ground water can be sampled for the presence of pesticides, herbicides, toxins, carcinogens, and other chemicals and pathogens.

In agriculture, plant seed stock can be selectively sampled for the presence of disease. In addition, irrigation water may be sampled for the presence of plant pathogens and chemicals that may be hazardous to humans.

In another application, the presence of a chemical in the air is identified. For example, the presence of air pollutants such as sulfur compounds can be determined based on their interactions with sensor gate materials. Chemical alteration of the gate material can be detected through contact potential modification, which exhibits itself as a pseudo gate voltage.

In yet another application, vapor concentrations in a sample can be monitored. Here, the gate insulator material and gate material are selected to control the response time to a pre-selected value. For example, a sensor may be utilized as a humidity sensor by incorporating a very thin oxide layer. In a particular embodiment the oxide may be from about 50 to about 100 angstroms thick where moisture affects the Si surface region. Other preselected gate materials may be altered to provide the sensor stimulus.

Although the foregoing invention has been described in terms of certain preferred embodiments, other embodiments will be apparent to those of ordinary skill in the art and the skilled artisan will be able to readily adapt the disclosed methods and sensors to a particular use. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

I claim:

1. A sensor for detecting the presence of a positively or negatively charged target in a sample comprising an active region of a field effect transistor (FET) overlying a buried conducting channel connecting a source region and a drain region, wherein the active region comprises multiple target recognition elements dispersed in a material matrix, and wherein the source and drain are p$^+$ and the buried conducting channel is a p-channel or the source and drain are n$^+$ and the buried conducting channel is an n-channel to provide an ohmic contact to a channel.

2. The sensor of claim 1, wherein the material matrix is a gel.

3. The sensor of claim 1, wherein the buried channel is a p-channel or an n-channel.

4. The sensor of claim 1, wherein the active region comprises a gate.

5. The sensor of claim 4, wherein the gate comprises a semiconducting material.

6. The sensor of claim 4, wherein the active region comprises a polysilicon gate.

7. The sensor of claim 4, wherein the gate comprises a conducting material.

8. The sensor of claim 1, wherein the active region comprises a gate dielectric layer.

9. The sensor of claim 1, wherein the gate dielectric layer is a silicon nitride layer of sufficient thickness to block unwanted sample effects including moisture.

10. The sensor of claim 9, wherein the silicon nitride layer is about 3000 Angstroms thick.

11. The sensor of claim 1, additionally comprising a back gate or side gate.

12. The sensor of claim 11, wherein the sensitivity of the sensor is increased by applying a bias to the back gate or side gate.

13. The sensor of claim 1, wherein the recognition element is selected from the group consisting of polypeptides, nucleic acids, inorganic molecules and organic molecules.

14. The sensor of claim 13, wherein the recognition element is selected from the group consisting of antibodies, nucleic acids, inorganic molecules and organic molecules.

15. The sensor of claim 1, wherein each of the recognition elements is specific for the same target.

16. The sensor of claim 1, wherein two or more recognition elements are specific for different targets.

17. The sensor of claim 16, wherein the number of each type of recognition element is such that the signal for binding of any of the targets is of approximately the same magnitude.

18. The sensor of claim 16, wherein the number of each type of recognition element is approximately equal and the recognition elements are readily saturated so that differences in the measured signal allow the identity of the present target or targets to be determined.

19. The sensor of claim 1, wherein the sensor operates in accumulation mode upon binding of a target.

20. The sensor of claim 1, wherein the sensor operates in depletion mode upon binding of a target.

21. An array comprising two or more of the sensor of claim 1.

22. The array of claim 21 comprising two or more sensors for detecting multiple targets.

23. The array of claim 22, comprising a first sensor for detecting the presence of a first target of interest and a second sensor for detecting the presence of a second target of interest.

24. The array of claim 23, wherein the presence of the second target of interest provides confirmation of the presence of the first target of interest.

25. The sensor of claim 1, further comprising secondary charged particles that contact bound targets to amplify their charge.

26. The sensor of claim 1, wherein the recognition elements further comprise orthogonal recognition elements.

27. The sensor of claim 1, wherein the density of the recognition elements is maximized to maximize sensor sensitivity.

28. The sensor of claim 1, wherein the active region is the minimum size necessary to produce a desired signal.

29. The sensor of claim 1, further comprising a protective material covering the area of the sensor outside of the active region to prevent unwanted interactions.

30. The sensor of claim 29, wherein the protective material is a biochemical layer that does not bind to components in the sample.

31. The sensor of claim 1, wherein targets are identified by chemical reaction with the gate material or a material deposited on the gate.

32. The sensor of claim 1, wherein the number of recognition elements is such that the production of any measurable signal corresponds to a particular concentration of a target in a sample.

33. The sensor of claim 1, further comprising linker molecules that attach recognition elements to the active region.

34. The sensor of claim 1, wherein the sensitivity of the sensor is tuned by channel doping.

* * * * *